(12) United States Patent
Pretto, Jr. et al.

(10) Patent No.: US 9,308,269 B2
(45) Date of Patent: Apr. 12, 2016

(54) STABLE LIQUID FORMULATIONS OF VOLATILE GAS ANESTHETICS

(75) Inventors: Ernesto Pretto, Jr., Coral Gables, FL (US); Camillo Ricordi, Miami, FL (US); Kyota Fukazawa, Ridgewood, NJ (US); Antonello Pileggi, Aventura, FL (US); Christopher Fraker, Hollywood, FL (US)

(73) Assignee: UNIVERSITY OF MIAMI, Miami, FL (US)

(*) Notice: Subject to any disclaimer, the term of this patent is extended or adjusted under 35 U.S.C. 154(b) by 0 days.

(21) Appl. No.: 14/235,372

(22) PCT Filed: Jul. 26, 2012

(86) PCT No.: PCT/US2012/048294
§ 371 (c)(1),
(2), (4) Date: Apr. 15, 2014

(87) PCT Pub. No.: WO2013/016511
PCT Pub. Date: Jan. 31, 2013

(65) Prior Publication Data
US 2014/0256828 A1    Sep. 11, 2014

Related U.S. Application Data

(60) Provisional application No. 61/512,096, filed on Jul. 27, 2011, provisional application No. 61/536,757, filed on Sep. 20, 2011.

(51) Int. Cl.
| | | |
|---|---|---|
| *A61K 31/08* | (2006.01) | |
| *A61K 47/34* | (2006.01) | |
| *A61K 9/00* | (2006.01) | |
| *A61K 47/10* | (2006.01) | |
| *A61K 9/107* | (2006.01) | |
| *A61K 47/44* | (2006.01) | |
| *A61K 31/60* | (2006.01) | |
| *A61K 31/045* | (2006.01) | |
| *A61K 31/01* | (2006.01) | |

(52) U.S. Cl.
CPC ............. *A61K 47/34* (2013.01); *A61K 9/0019* (2013.01); *A61K 9/1075* (2013.01); *A61K 31/08* (2013.01); *A61K 31/60* (2013.01); *A61K 47/10* (2013.01); *A61K 47/44* (2013.01); *A61K 31/01* (2013.01); *A61K 31/045* (2013.01)

(58) Field of Classification Search
CPC .... A61K 31/01; A61K 31/045; A61K 9/0019
USPC ........................................................ 514/722
See application file for complete search history.

(56) References Cited

U.S. PATENT DOCUMENTS 5,478,860 A    12/1995    Wheeler et al.
6,623,765 B1    9/2003    Dennis et al.
9,000,048 B2 *    4/2015    Mecozzi et al. ............. 514/722
2005/0129754 A1    6/2005    Gray
2008/0234389 A1    9/2008    Mecozzi
2011/0039944 A1    2/2011    Capelli et al.

OTHER PUBLICATIONS

Hitachi High-Tech; Hitachi High-Performance Liquid Chromatograph LaChrom Elite: System Architecture; http://www.hitachi-hitec.com/global/science/lc/elite_smash.html; (Jun. 30, 2011).
BASF Product Information the Chemicals Catalog, Pluronic F127; http://worldaccount.basf.com/wa/NAFTA~en_US/Catalog/ChemicalsNAFTA/info/BASF/PRD/30; (Jun. 27, 2011).
Hank's Balanced Salt Solution, 1X-Hank's Balanced Salt Solution-Buffered Salt Solutions; CELLGRO; http://cellgro.com/products/balanced-salt-solutions/hand-s-balance-salt-solution/hank-s-balanced (Jun. 27, 2011).
PUBMED, http://www.ncbi.nlm.nih.gov/pubmed/2124564; Histamine release associated with intravenous delivery of a fluorocarbon-based sevoflurane emulsion in canines (Apr. 18, 2011).
Flamproof Stirrers, Homogenizers & Emulsifiers; Laboratory Stirrers, Laboratory Instruments, Remi Laboratory Instruments; http://www.remilabworld.com/AC_Stirrers_Emulsifiers_Homogenizers.asp (Jul. 1, 2011).
Microfluidics 110T Emulsifer—Cell Disrupters/Harvesters—American Instrument Exchange (AIE) Item 1240P Cell Dis—Microfluidics 1105 Emulsifer; http://www.americaninstrument.com/equipment/Cell-Disrupters-Harvesters/1240P-cell (Jul. 1, 2011).
Shanghai Jingke Scientific Instrument Co., Ltd; Products Catalog: JK-HSE-1 High, http://jingxuecoltd.itrademarket.com/2208389/jk-hse-1-high-shear-emulsifier.htm (Jul. 1, 2011).
ALT American Laboratory Trading, Inc.; Fisher Scientific F 550 Sonic Dismembrator; http://www.americanlaboratorytrading.com/product-details-Fisher-Scientific--12125.html (Jul. 1, 2011).
Fisher Scientific; Model 505 Sonic Dismembrator; http://www.fishersci.com/ecomm/servlet/fsproductdetail?storeId=10652&productId=13101105&c . . . (Jun. 30, 2011).
3M, Fluorinert, Electronic Liquid FC-43 , Product Information, Performance Materials (May 2000).
Technical Bulletin, BASF The Chemical Company, Pluronic F127, Block Copolymer Surfactant, Performance Chemicals (2004).
Technical Bulletin, BASF The Chemical Company, Pluronic F68, Block Copolymer Surfactant, Performance Chemicals (2004).
BASF ExAct, p. 5—No. 3, Nov. 1999, Poloxamers (1), Lutrol F68 (Poloxamer 188) B. Fussnegger.
Intralipid Official FDA Information, side effects and uses; http://www.drugs.com/pro/intralipid.html (Jun. 29, 2011).
drugs.com; Intralipid; http://www.drugs.com/pro/intralipid.html?printable=1 (May 2, 2011).
BASF Product Information the Chemicals Catalog, Pluronic F 68; http://worldaccount.basf.com/wa/NAFTA~en_US/Catalog/ChemicalsNAFTA/info/BASF/PRD/30 . . . ; (Jun. 27, 2011).

* cited by examiner

Primary Examiner — Kevin E Weddington
(74) Attorney, Agent, or Firm — Marshall, Gerstein & Borun LLP

(57) ABSTRACT

A stable liquid nanoemulsion of a volatile gas anesthetic, such as, isoflurane or sevoflurane, is disclosed which is effective in inducing and maintaining a state of anesthesia and/or general anesthesia in a patent. A method of preparation of stable liquid formulations of volatile gas anesthetics is presented, as well as a method for directly testing the concentration of a volatile gas anesthetic in a stable liquid formulation. A kit comprising an amount of a stable liquid formulation of a volatile gas anesthetic, and the non-specialized equipment for administration of the same to a patient, either in an operating room environment or in the field, is also described herein.

15 Claims, 31 Drawing Sheets

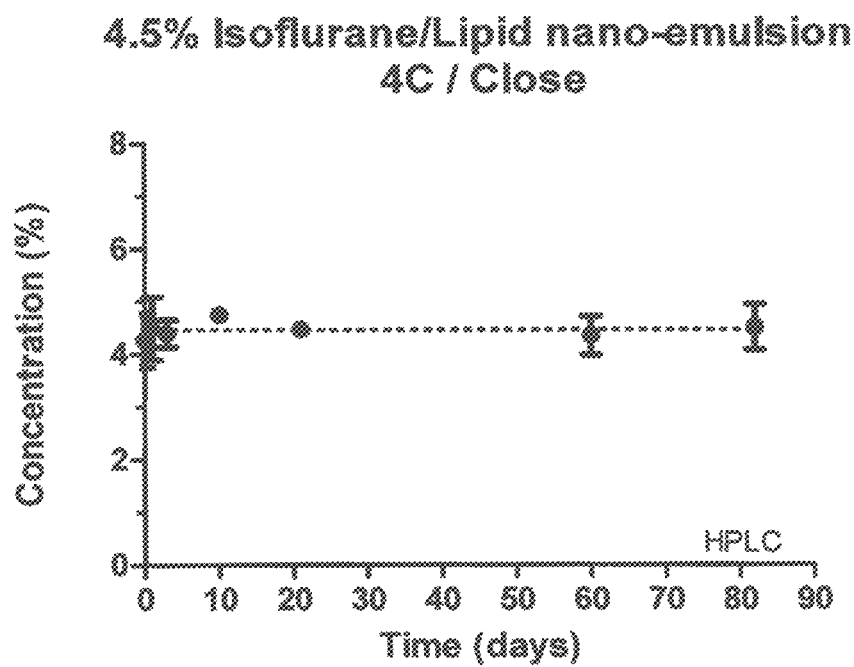
FIGURE 2Av2 Shelf-life studies (Days) for 4.5% Isoflurane/Lipid emulsion (Close) at 4C by High performance Liquid Chromatography (HPLC)

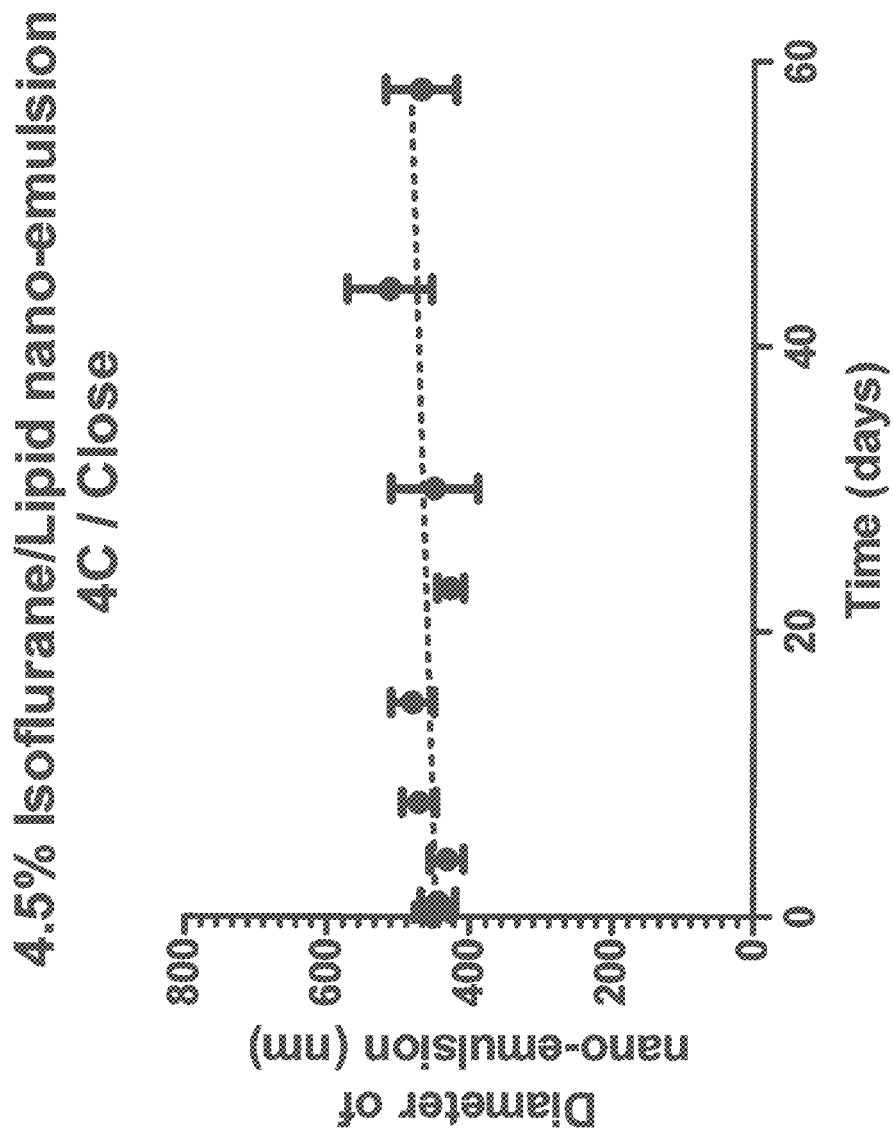
FIGURE 4A Shelf-life studies (Days) for 4.5% Isoflurane/Lipid emulsion (Close) at 4C by direct light scattering (DLS)

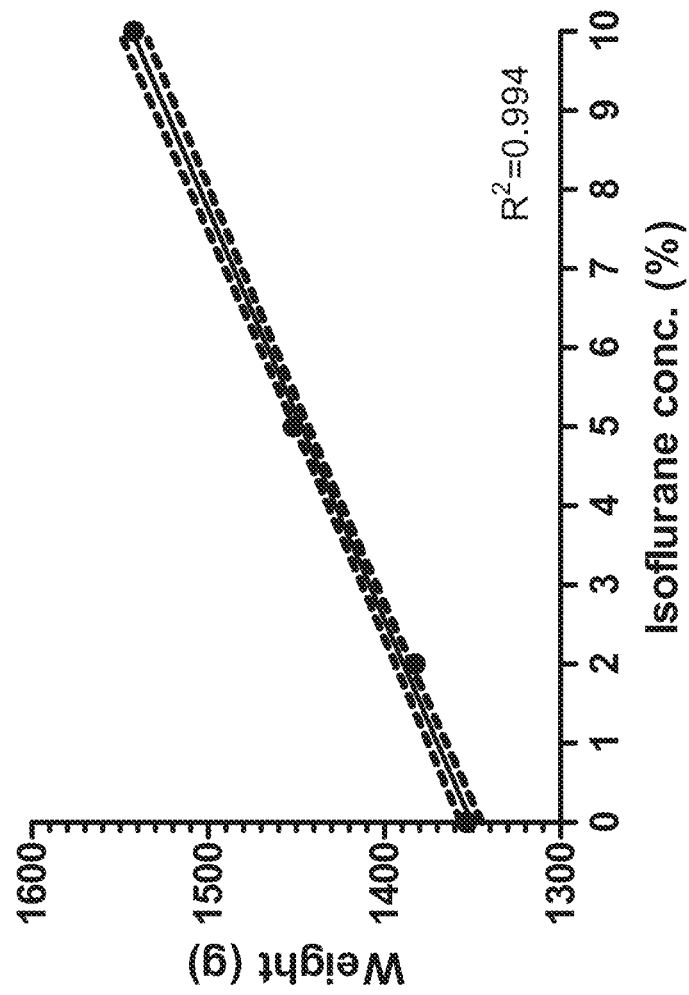
FIGURE 8  Standard curve for determination of isoflurane concentration by weight

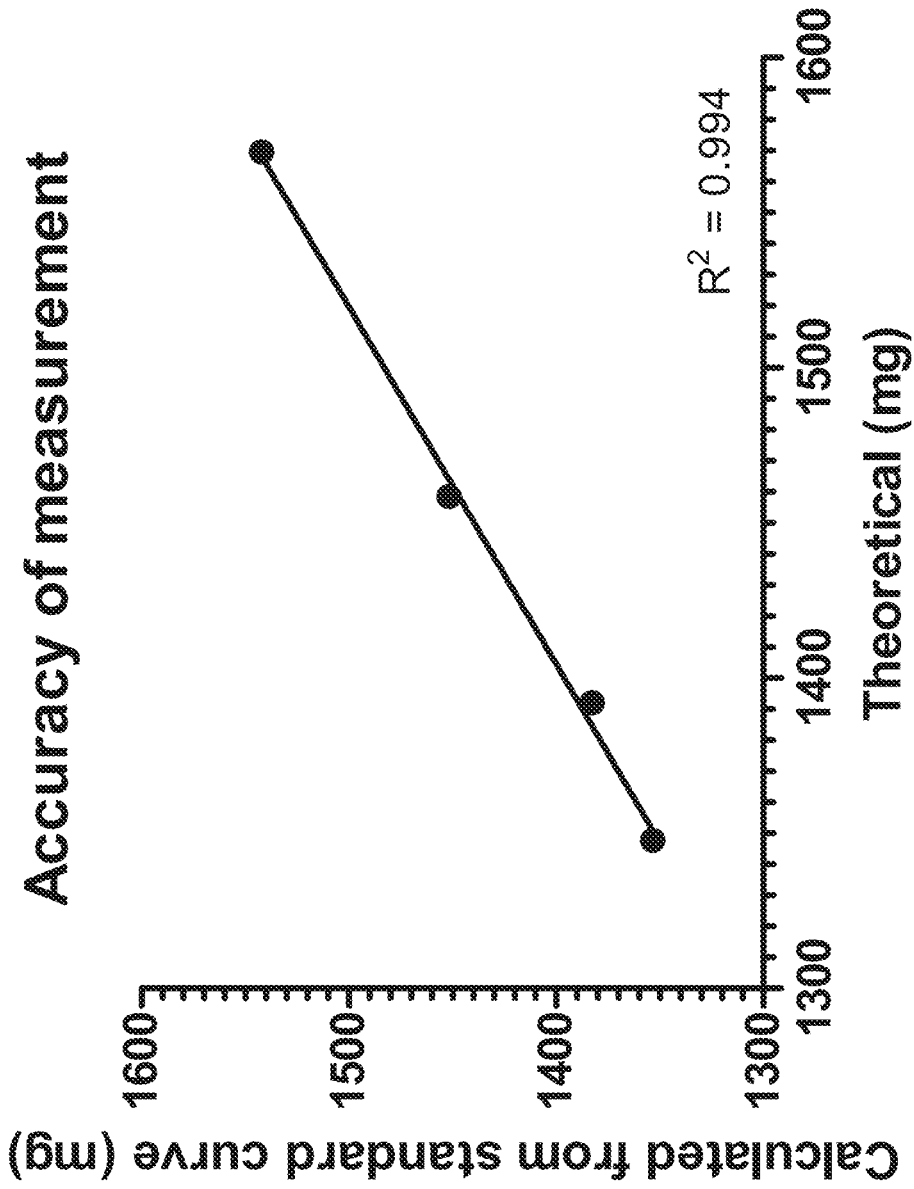
FIGURE 9  Accuracy of measurement by weight

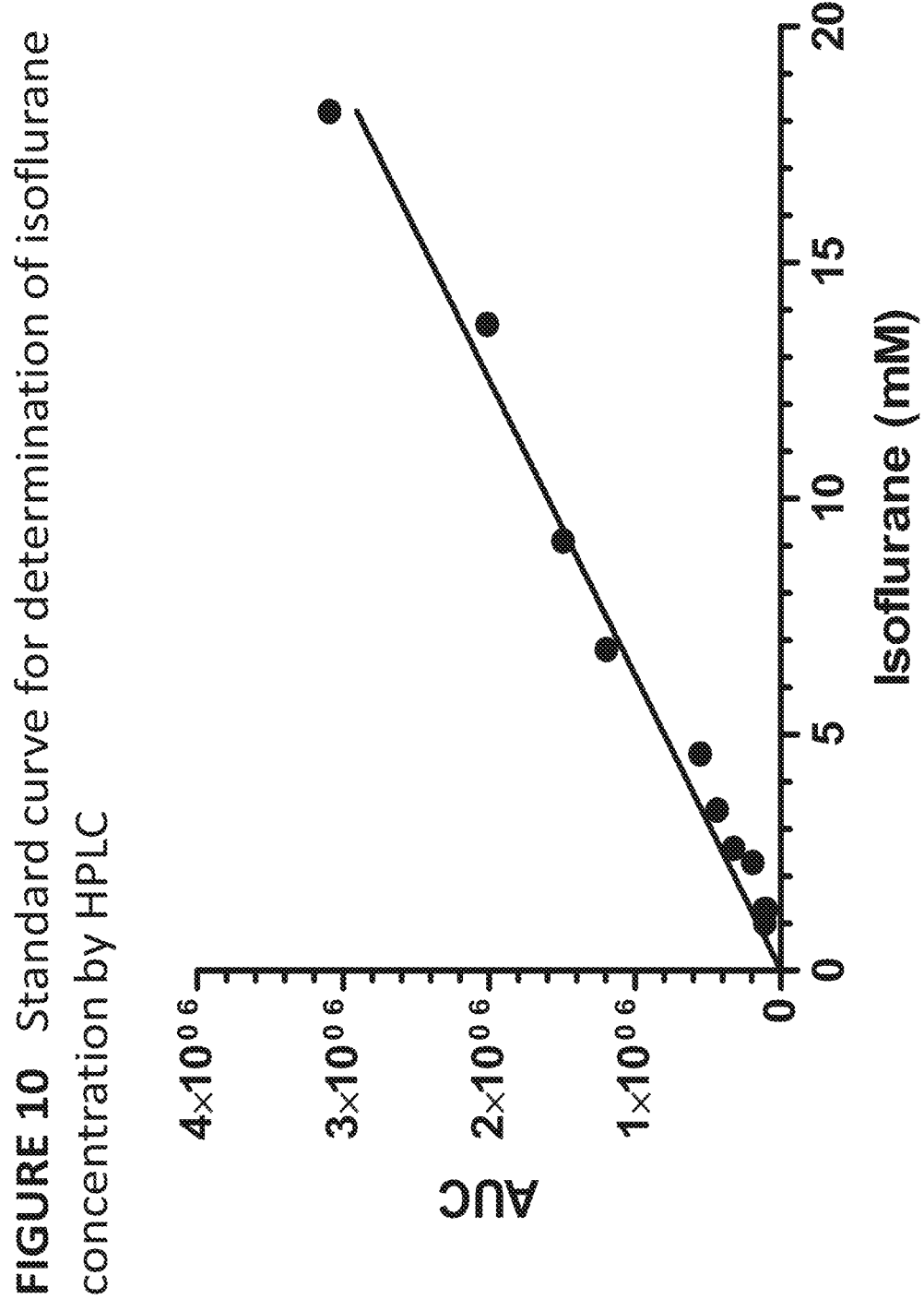
FIGURE 10 Standard curve for determination of isoflurane concentration by HPLC

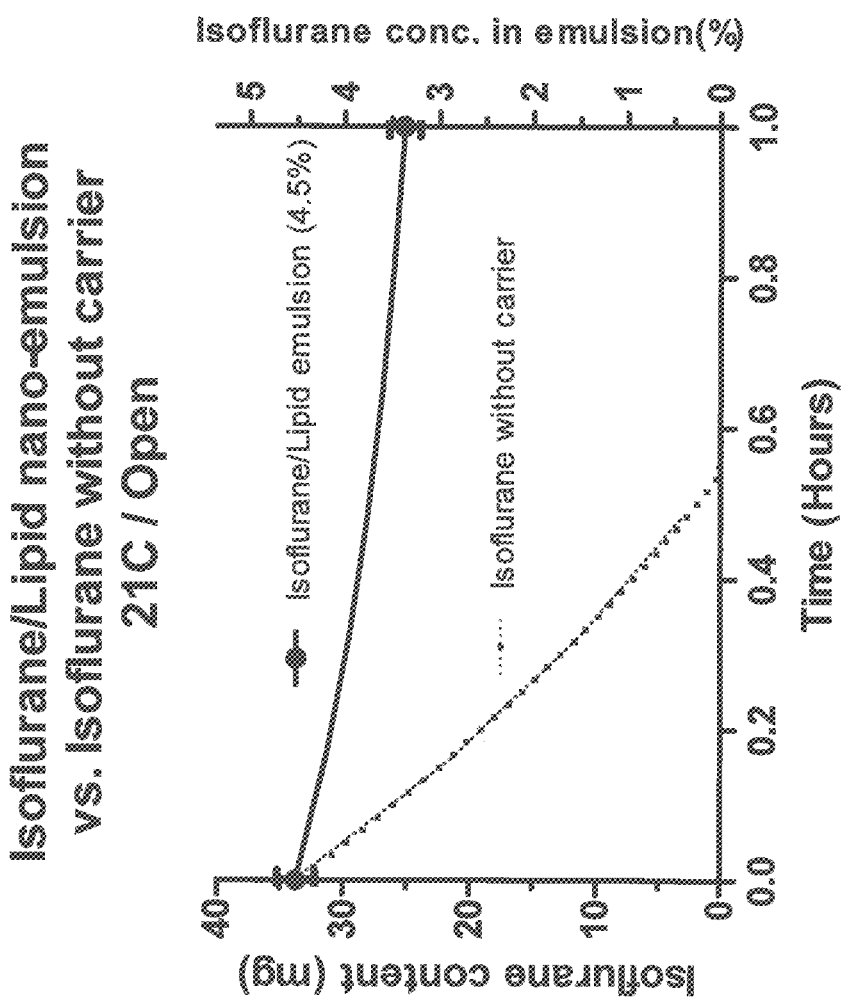
FIGURE 11 Comparison of isoflurane content in 4.5% Isoflurane/Lipid emulsion vs. Isoflurane without carrier (Open) at 21C by weight

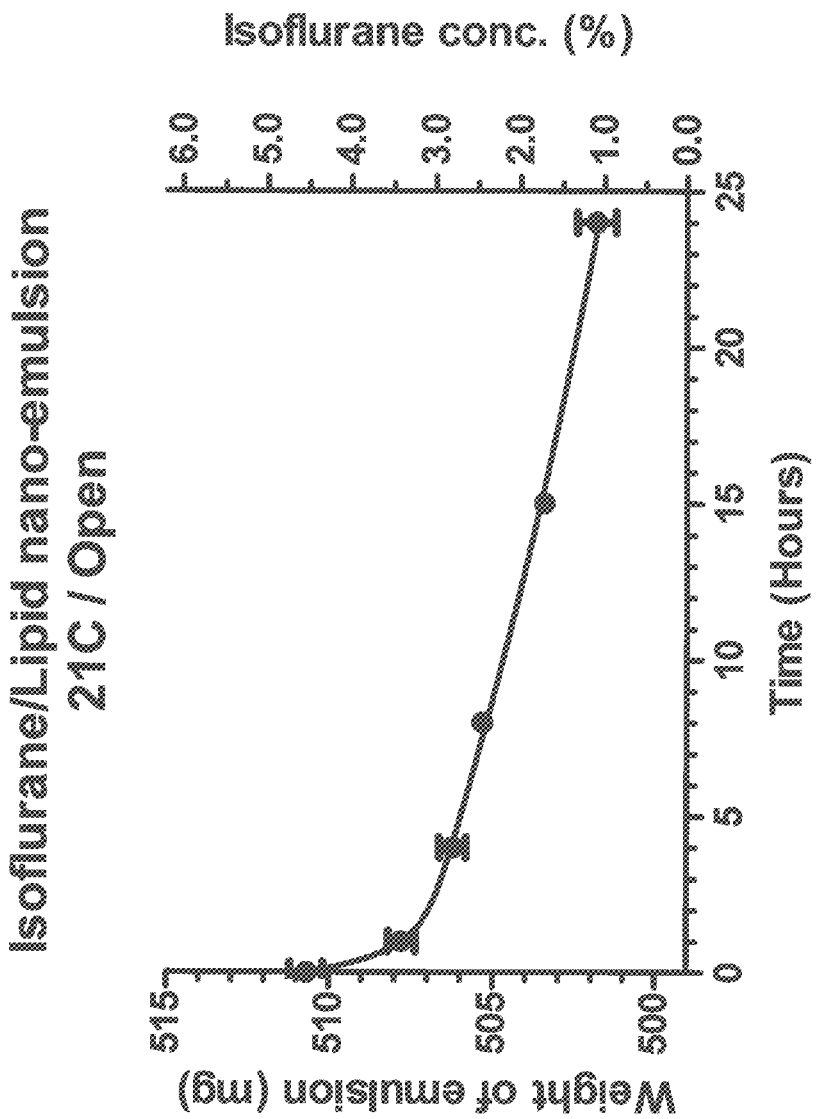
FIGURE 12 Stability study (hours) for 4.5% Isoflurane/Lipid emulsion (Open) at 21.6C by weight

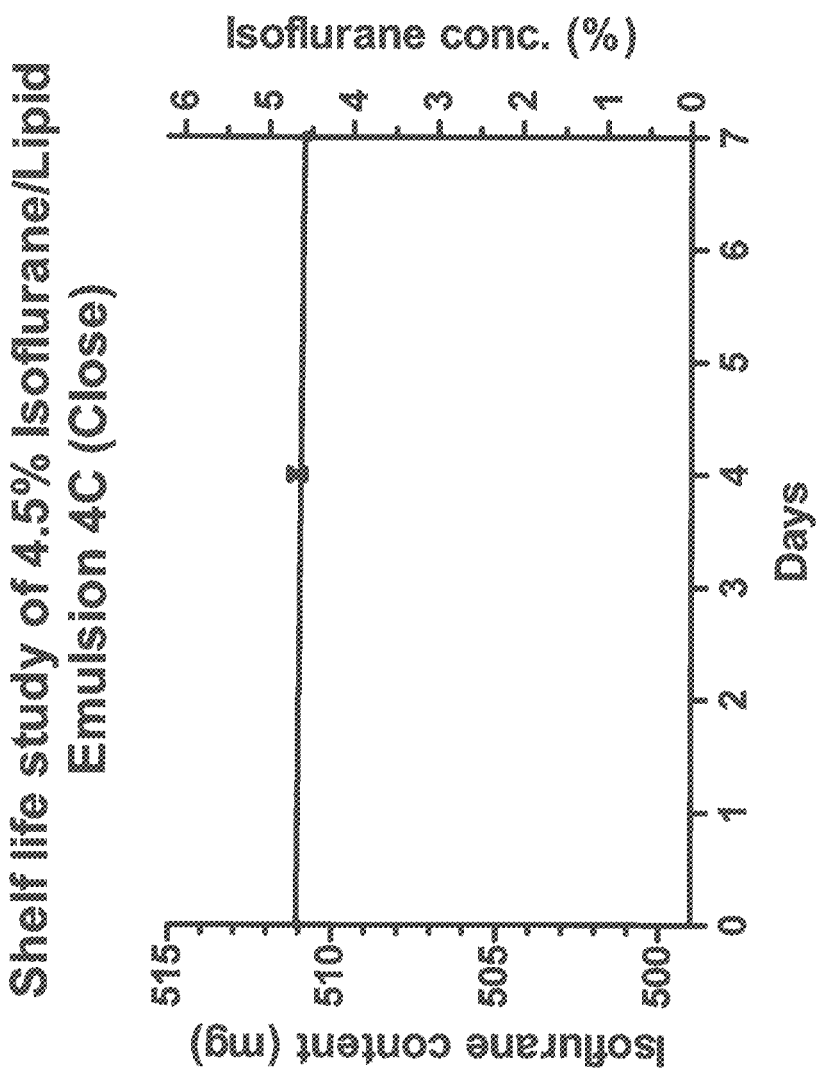
FIGURE 13 Shelf-life studies (Days) for 4.5% Isoflurane/Lipid emulsion (Close) at 4C by Weight

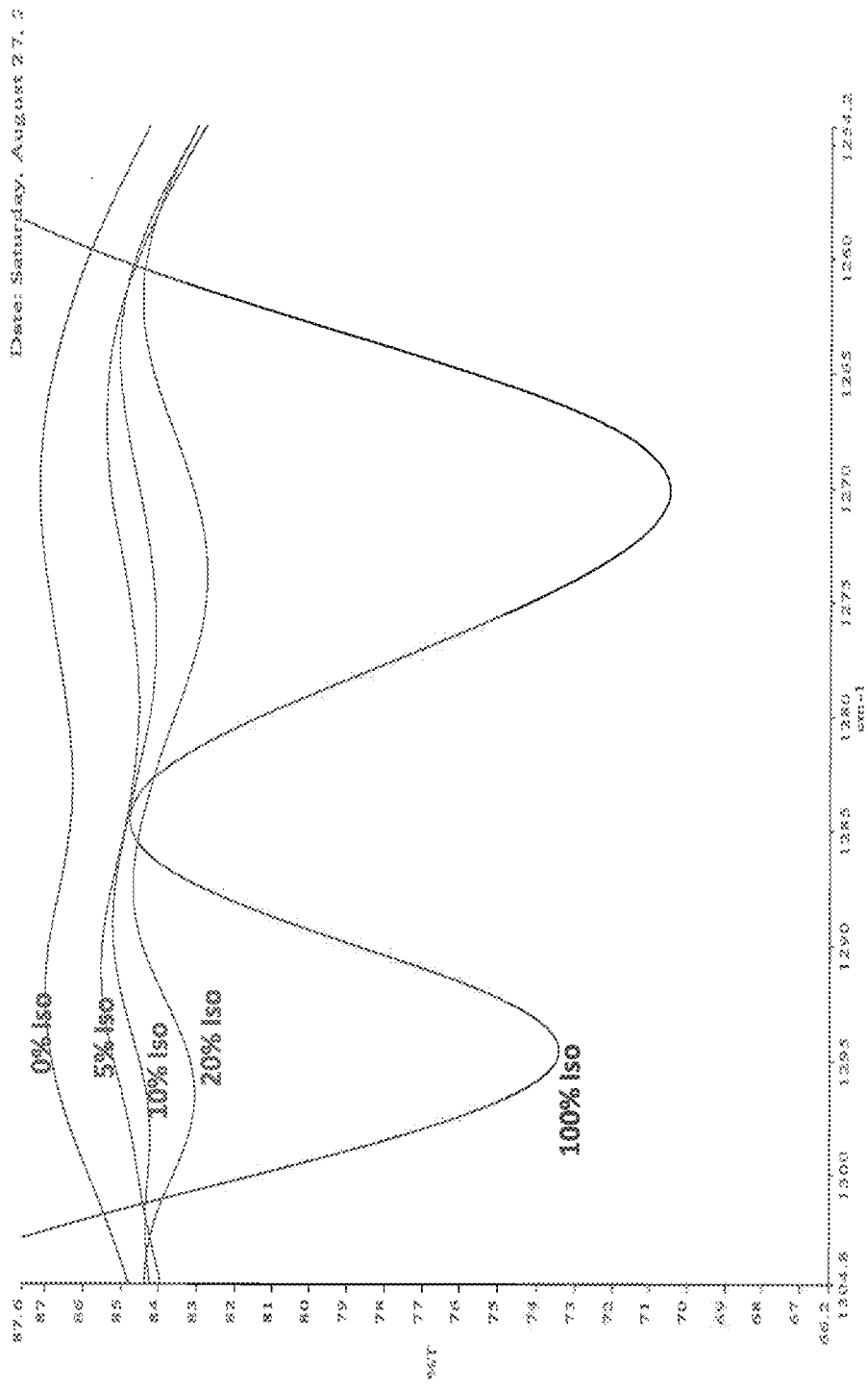
FIGURE 14 Standard curve for determination of isoflurane concentration by ATR-FTIR

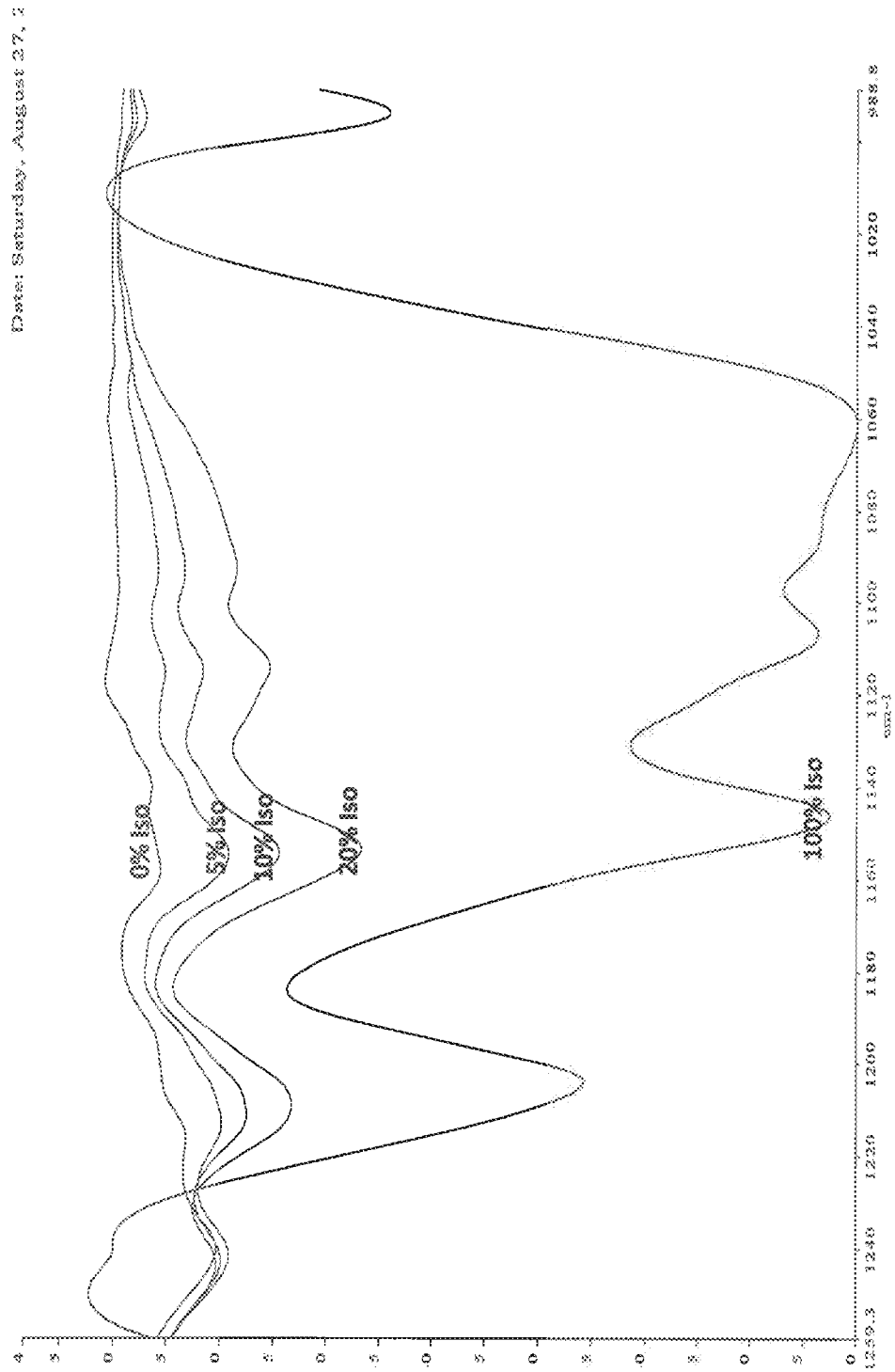
FIGURE 15 Standard curve for determination of isoflurane concentration by ATR-FTIR

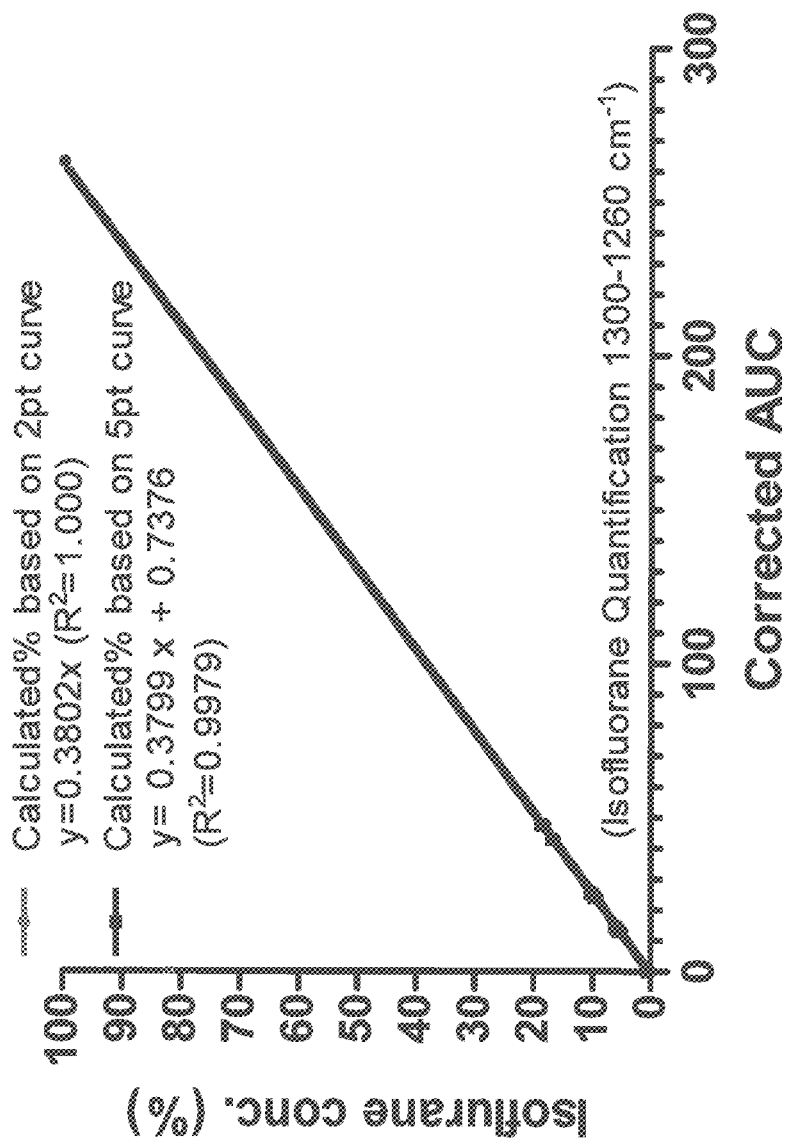
FIGURE 16 Standard curve for determination of isoflurane concentration by ATR-FTIR (1300-1260cm$^{-1}$)

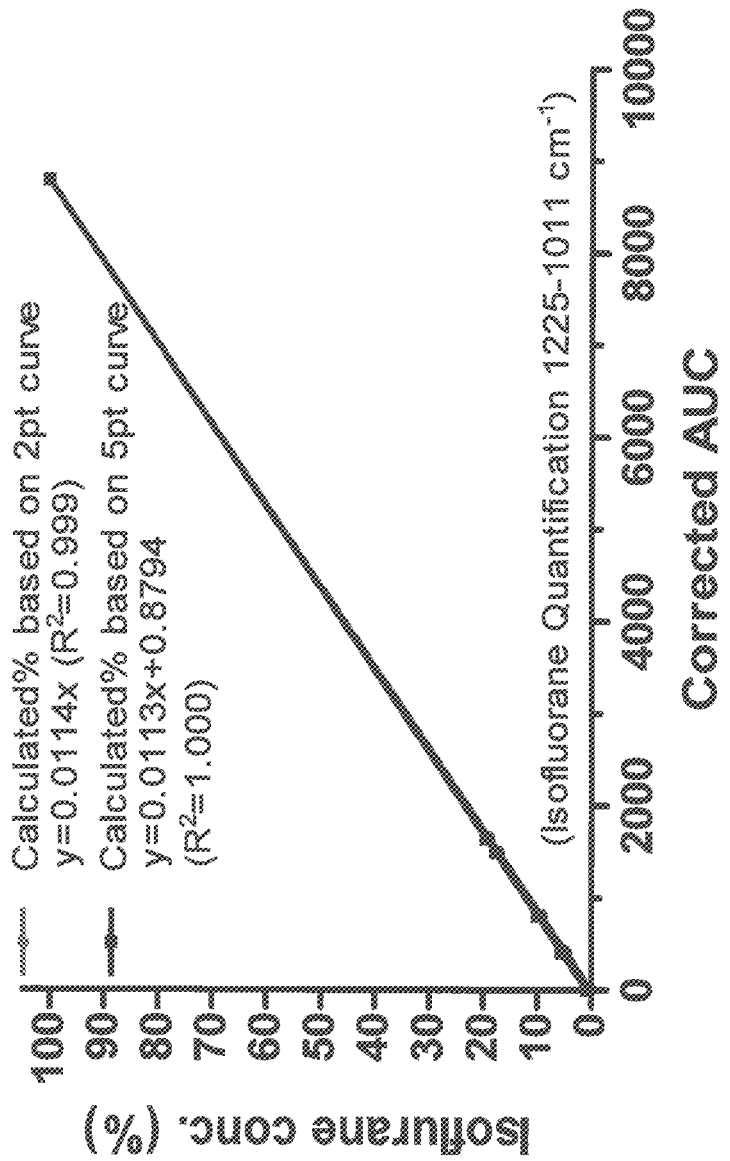
FIGURE 17 Standard curve for determination of isoflurane concentration by ATR-FTIR (1225-1011cm$^{-1}$)

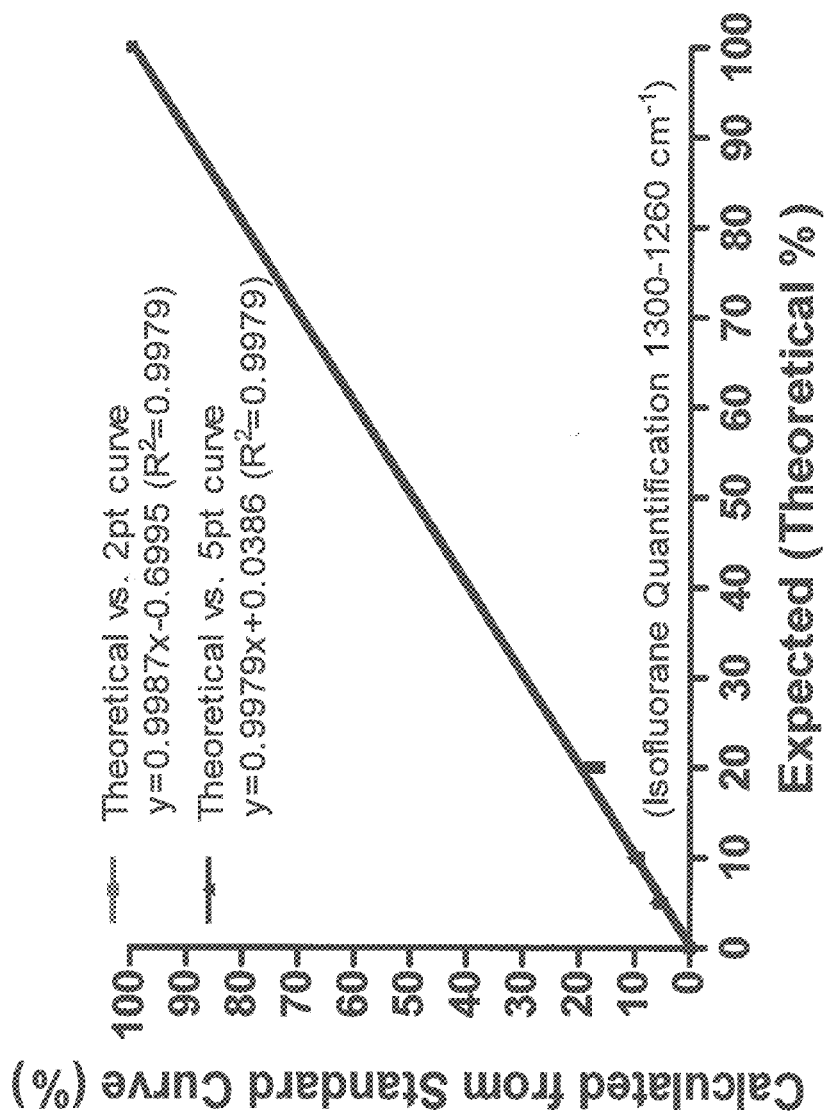
FIGURE 18 Standard curve for determination of isoflurane concentration by ATR-FTIR (1300-1260cm$^{-1}$)

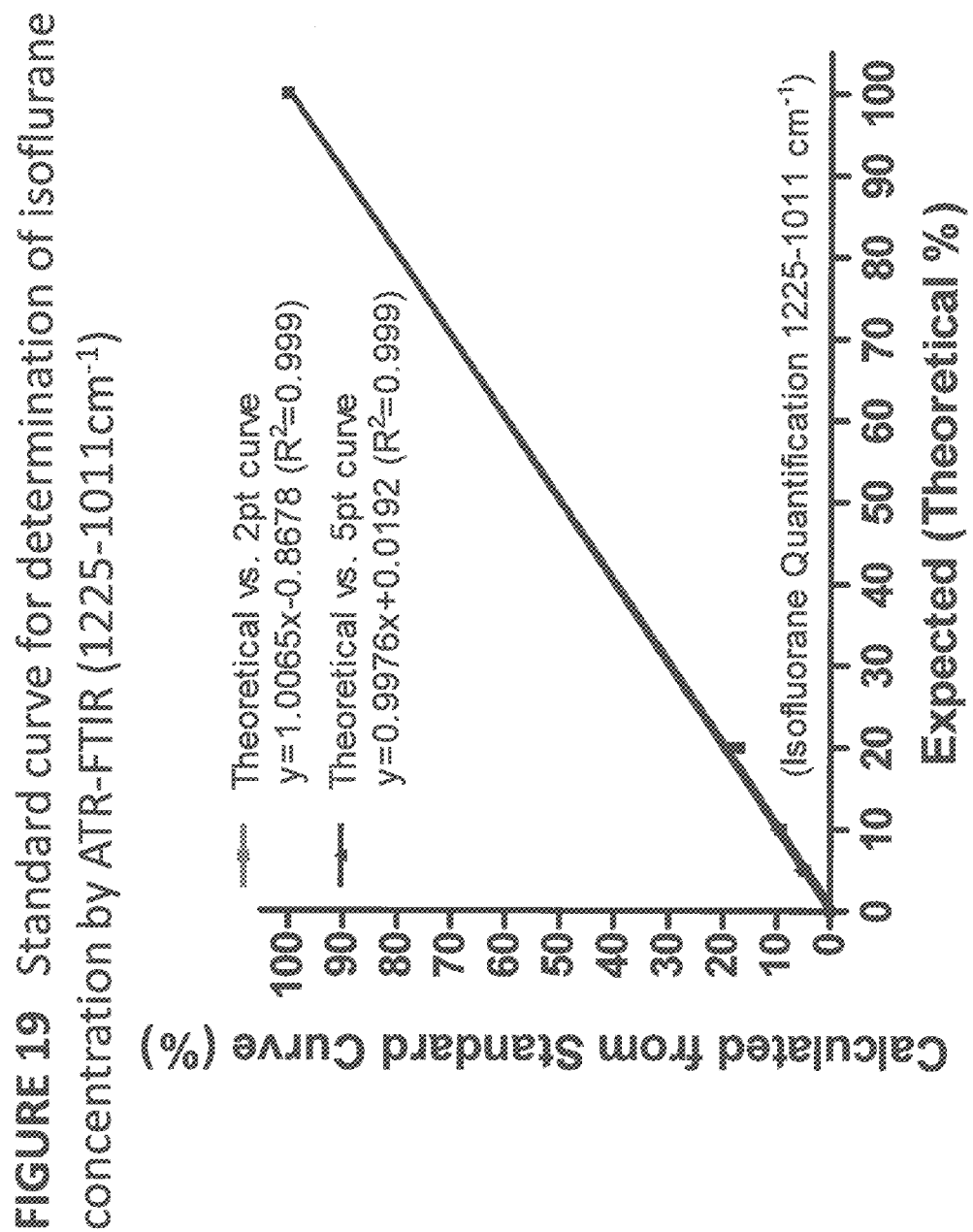
FIGURE 19 Standard curve for determination of isoflurane concentration by ATR-FTIR (1225-1011cm$^{-1}$)

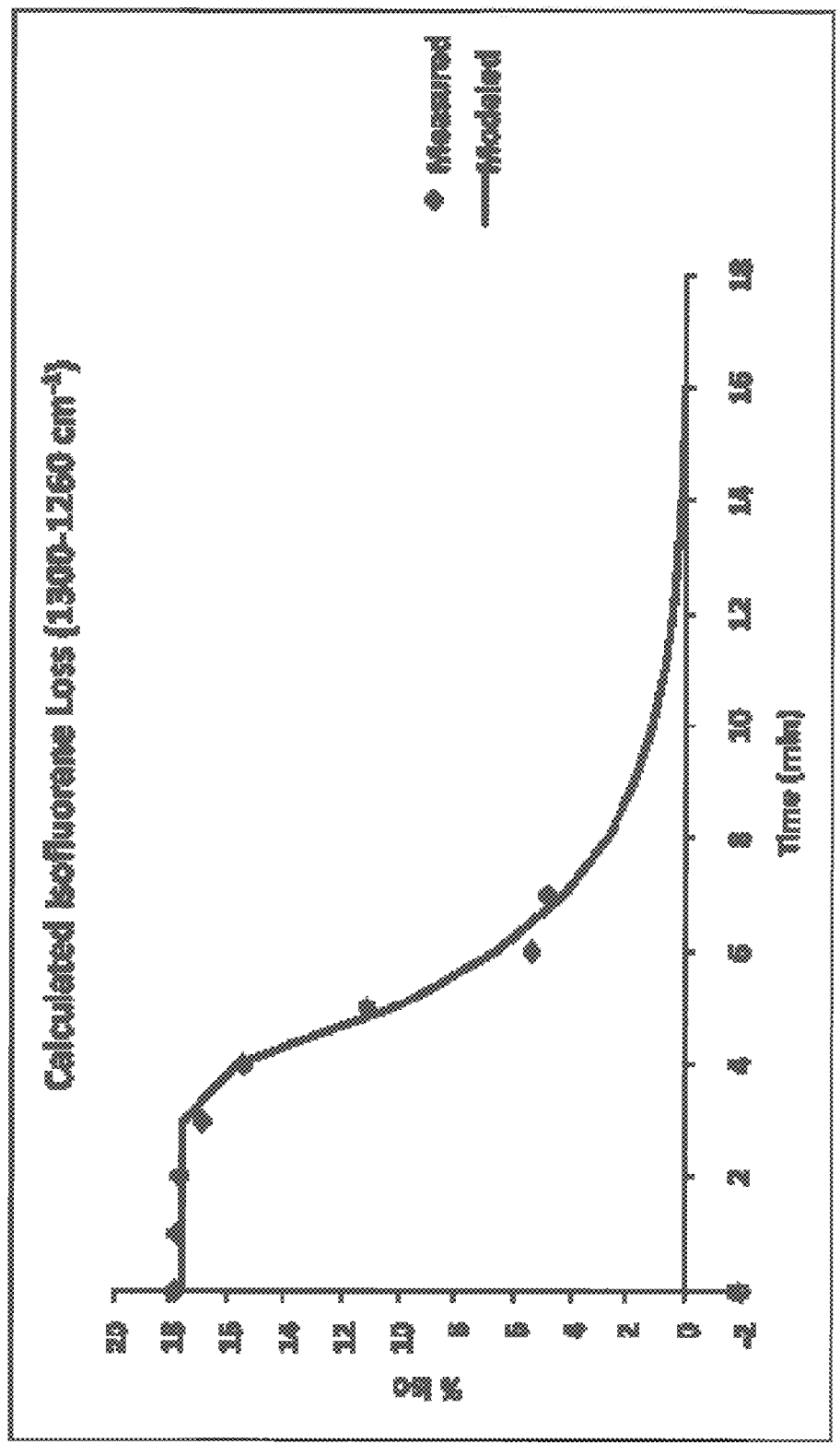
FIGURE 20 Modeled vs. Measured isoflurane loss over time by ATR-FTIR (1300-1260cm$^{-1}$).

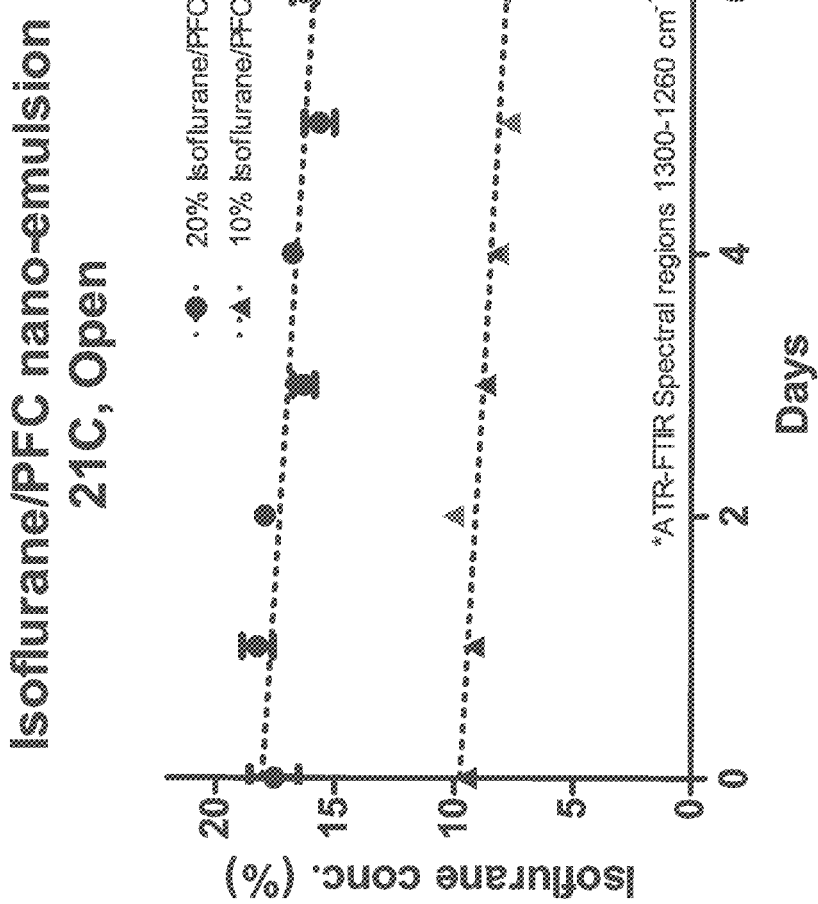
FIGURE 20A Stability study (days) for 20% and 10% Isoflurane/PFC emulsion (Open) at 25C by ATR-FTIR

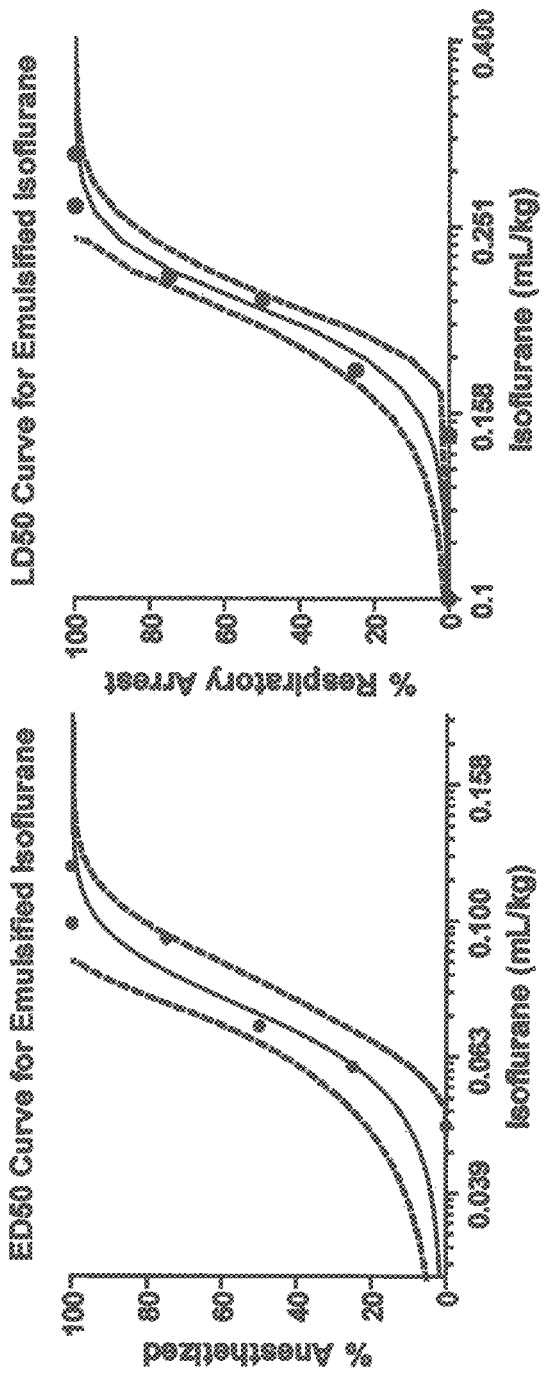
FIGURES 21A & 21B In-vivo Study to Determine Anesthetic Potency and Safety of 4.5% Isoflurane/Lipid Nano-Emulsion (ED50/LD50)

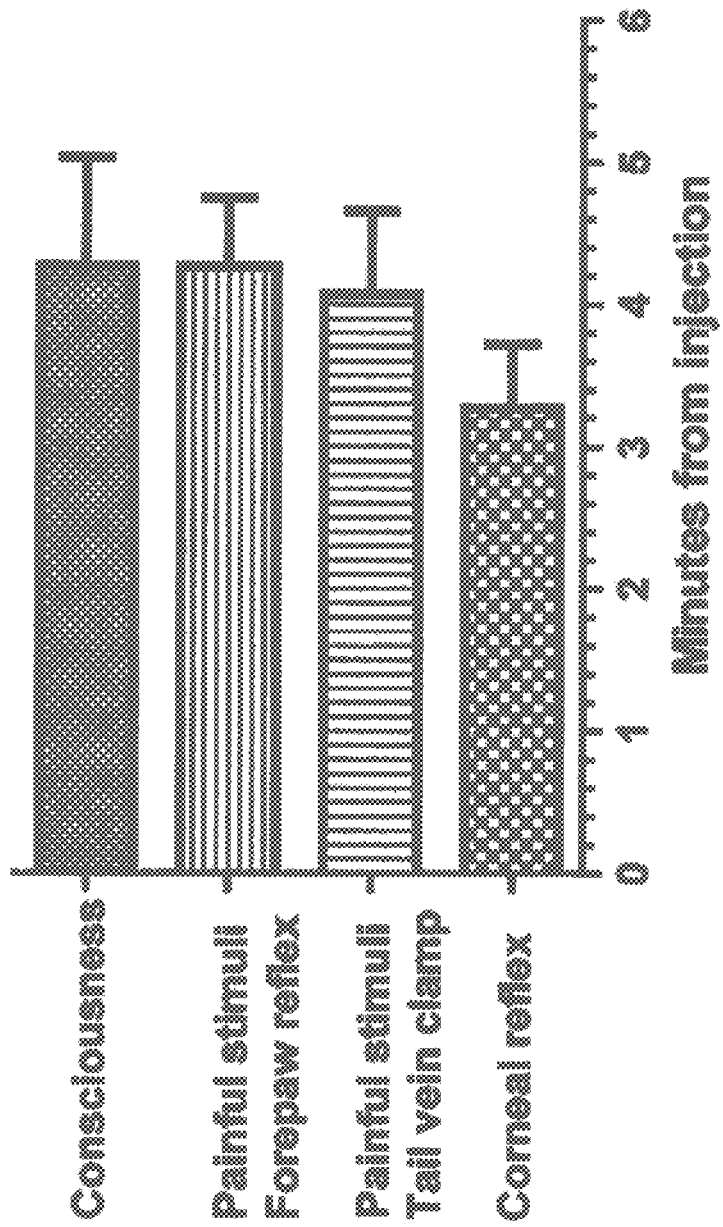
FIGURE 22  In-Vivo Study: Duration of Induction after injection of 4.5% Isoflurane/Lipid Emulsion

FIGURE 23 Duration of induction of 4.5% Isoflurane/Lipid emulsion as anesthetic agent (in-vivo)

| Rat | Weight | Dose of anesthetics | Time to induction | Time to recovery | | | |
|---|---|---|---|---|---|---|---|
| | | | | Consiousness | Paw reflex | Tail clamping | Corneal reflex |
| | g | mL<sub>ISO</sub>/kG | min | min | min | min | min |
| 1 | 258 | 0.177 | 2.725 | 4.275 | 4.275 | 4.275 | - |
| 2 | 254 | 0.190 | 2.975 | 4.025 | 4.025 | 4.025 | 4.025 |
| 3 | 263 | 0.228 | 3.626 | 3.374 | 3.374 | 3.374 | 2.374 |
| 4 | 245 | 0.210 | 3.407 | 2.593 | 3.593 | 2.593 | 2.593 |
| 5 | 249 | 0.183 | 2.917 | 7.083 | 6.083 | 6.083 | 4.083 |
| Average | | 0.198 ± 0.021 | 3.130 ± 0.373 | 4.270 ± 1.702 | 4.270 ± 1.073 | 4.070 ± 1.300 | 3.269 ± 0.912 |

FIGURE 24 Histologic studies after in vivo injection of anesthetic dosage of 4.5% Isoflurane/lipid emulsion

| | Control Naïve | Carrier only | Isoflurane (1) | Isoflurane (2) | Isoflurane (3) | Isoflurane (4) |
|---|---|---|---|---|---|---|
| Brain | Normal | Normal | Normal | Normal | Normal | Normal |
| Heart | Normal | Normal | Normal | Normal | Normal | Normal |
| Lung - Atelectasis | Normal | Normal | (+) | Normal | Normal | (+) |
| Interstitial Inflammation | Normal | Normal | (+) | Normal | Normal | (+) |
| Liver - Sinusoidal Dilatation | Normal | Normal | (+) | (+) | (+) | (+) |
| Focal Micro/Macrosteatosis | Normal | Normal | Mild | Mild | Mild | Mild |
| Mixed Portal Triaditis | Normal | Mild | Mild | Mild | Normal | Mild |
| Kidney - ATN | Normal | Normal | (+) | (+) | (+) | (+) |
| Vascular Congestion | (+) | Normal | | | | |

FIGURE 25 Laboratory testing after in vivo injection of anesthetic dosage of 4.5% Isoflurane/lipid emulsion

|  | Control Naïve | Carrier only | Isoflurane (1) | Isoflurane (2) | Isoflurane (3) | Isoflurane (4) |
|---|---|---|---|---|---|---|
| Dosage (mL) | - | - | 1.63 | 1.67 | 2.15 | 1.44 |
| Weight (g) | 384 | 408 | 348 | 360 | 369 | 384 |
| Hemolysis Index | 0 | 3 | 0 | 0 | 0 | 0 |
| Lipemia Index | 0 | 2 | 1 | 1 | 1 | 1 |
| Glucose | 151 | 132 | 91 | 128 | 178 | 105 |
| BUN | 20 | 16 | 21 | 18 | 22 | 22 |
| CREA | 0.3 | 0.2 | 0.3 | 0.3 | 0.4 | 0.4 |
| BUN/Crea Ratio | 66.7 | 80.0 | 70.0 | 60.0 | 55.0 | 55.0 |
| Calcium | 9.7 | 7.3 | 8.6 | 8.3 | 7.8 | 8.0 |
| Phosphorus | 5.6 | 8.1 | 5.7 | 5.2 | 4.8 | 6.3 |
| Total Protein | 5.9 | 7.8 | 5.2 | 4.8 | 4.4 | 4.6 |
| Albumin | 3.2 | 3.9 | 2.3 | 2.2 | 1.9 | 1.9 |
| A/G Ratio | 1.19 | 1.00 | 0.79 | 0.85 | 0.76 | 0.70 |
| ALT | 47 | 54 | 50 | 45 | 51 | 47 |
| Alkaline Phosphatase | 241 | 126 | 178 | 158 | 145 | 176 |
| Total Bilirubin | 0.3 | 3.3 | 0.2 | 0.2 | 0.2 | 0.3 |

FIGURE 26 Experimental design of cytoprotective effect of isoflurane on pancreatic beta cells against oxidative stress induced apoptosis.
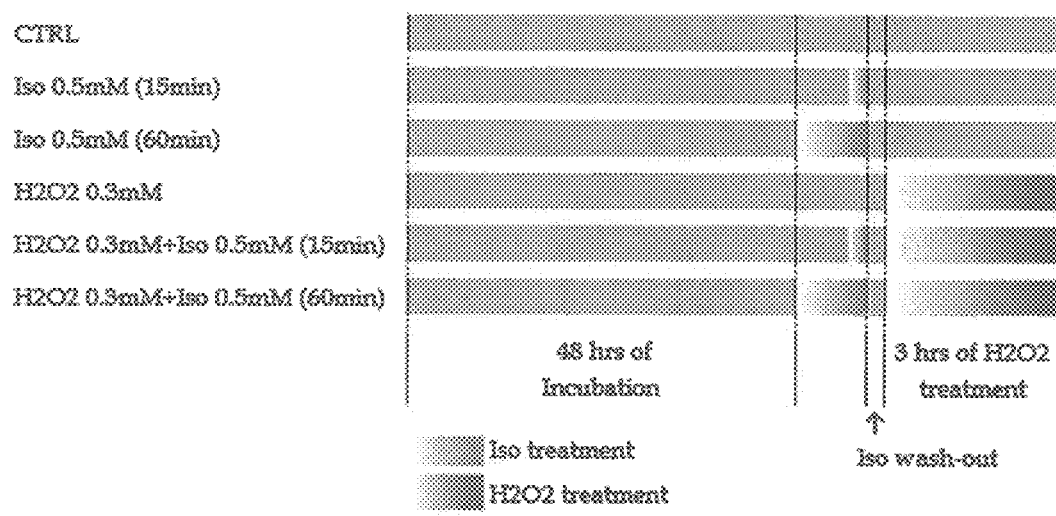

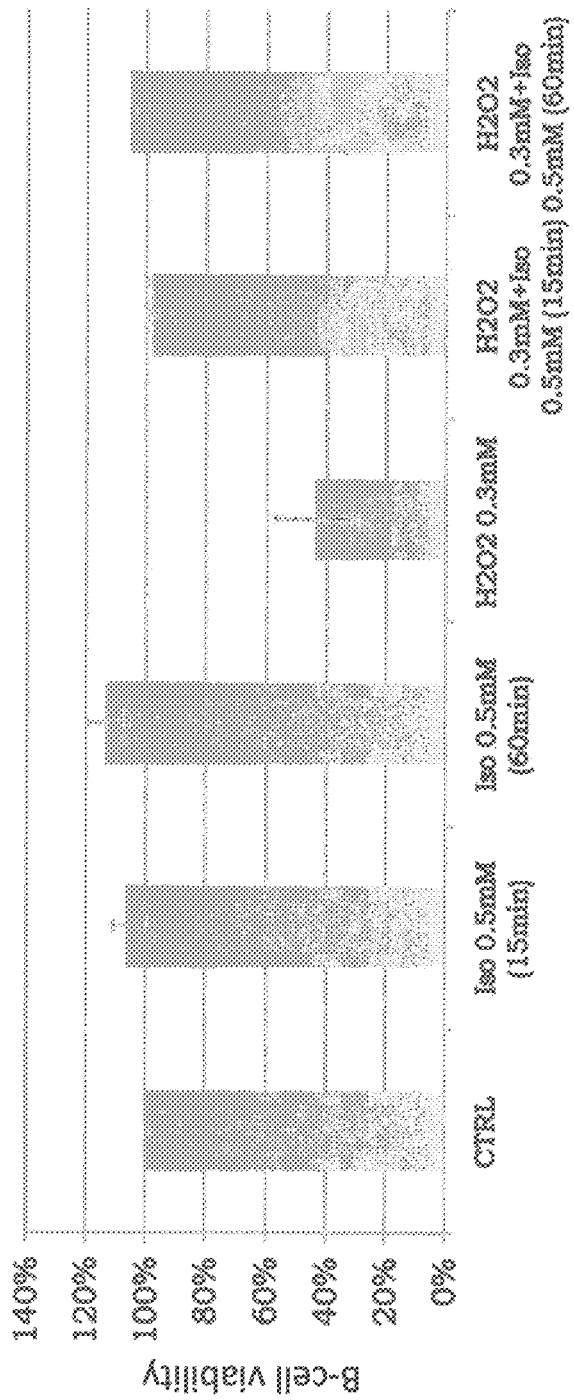
FIGURE 27 Effects of $H_2O_2$ and APC on beta-cell viability

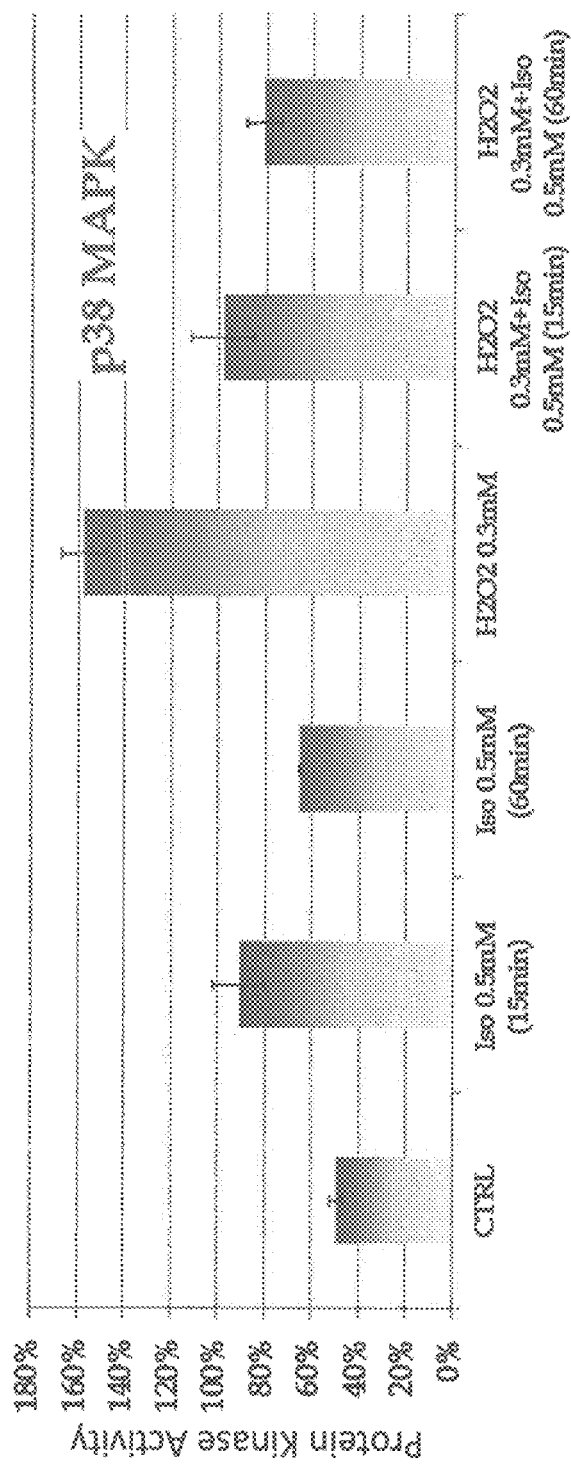
FIGURE 28  Effects of H₂O₂ and APC on beta-cell viability

STABLE LIQUID FORMULATIONS OF VOLATILE GAS ANESTHETICS

CLAIM OF PRIORITY

The present application is based on and a claim of priority is made to previously filed, U.S. provisional patent application having Ser. No. 61/512,096 filed on Jul. 27, 2011 and U.S. provisional patent application having Ser. No. 61/536,757 filed on Sep. 20, 2011 with the United States Patent and Trademark Office, which are incorporated herein by reference in its entirety.

STATEMENT REGARDING FEDERALLY-SPONSORED RESEARCH AND DEVELOPMENT

Not applicable.

BACKGROUND OF THE INVENTION

1. Field of the Invention

This invention relates generally to stable liquid formulations of volatile gas anesthetics. More in particular, the present invention comprises stable liquid nanoemulsions of volatile gas anesthetics, as well as methods of preparation, testing, and administration, such as, via injection.

2. Description of the Related Art

Volatile gas anesthetics include, among other compounds, a family of halogenated ethers that are highly hydrophobic liquids at room temperature, wherein the anesthetic potency is directly proportional to the lipid solubility of the volatile gas anesthetic. When exposed to ambient air, volatile gas anesthetics quickly evaporate depending on their temperature or latent heat of vaporization. The most commonly used volatile gas anesthetics at the present time are isoflurane, sevoflurane, and desflurane.

Currently, the only method of delivery, i.e., uptake and distribution, of vaporized volatile gas anesthetics is via inhalation into the lungs of a patient via a closed or open breathing circuit consisting of plastic tubing, face mask, laryngeal mask airway or endotracheal tube, producing induction and maintenance of an artificial, reversible state of unconsciousness or general anesthesia. The delivery of one or more volatile gas anesthetics via inhalation is currently widely used, however, this requires the use of expensive and specialized equipment and instrumentation to vaporize the volatile gas anesthetic, which is supplied in a liquid state, and to mix or dilute with other gases, such as, oxygen or compressed air, in order to yield therapeutic, but non-toxic concentrations of anesthetic(s). Instruments to detect and analyze concentrations of the anesthetic(s) in exhaled gas, such as infrared gas analyzers, are also used in conjunction with inhalation anesthesia.

Surgery requires anesthetic agents that can induce analgesia, anesthesia, and amnesia and muscle relaxation. Volatile gas anesthetics are complete anesthetics, that is, at low concentrations they provide sedation, amnesia and analgesia, while at higher concentrations they also induce unconsciousness or general anesthesia and muscle relaxation. Conventional intravenous anesthesia induction agents such as dexmedetomidine (precedex), ketamine, propofol, thiopental or etomidate (amidate) are hypno-sedatives or major tranquilizers that are used for sedation, amnesia or general anesthesia, but are not complete anesthetics because they do not have sufficient analgesic or muscle relaxation properties (Eger II, 2004).

Therefore, in order to achieve an acceptable state of anesthesia for surgery, the present state of the art involves the administration of combinations of intravenous agents, potent narcotic analgesics, neuromuscular relaxants, as well as inhaled volatile gas anesthetics, by trained anesthesiologists and anesthetists, in order to achieve all of the desired and/or required physiologic effects. Generally, intravenous agents are used to induce sleep, and then inhaled volatile gas anesthetics are provided to maintain the state of general anesthesia. Neuromuscular blocking agents are also used to potentiate muscle relaxation. Although induction and maintenance of general anesthesia can be done solely with some volatile gas anesthetics, induction of anesthesia via inhalation of volatile gas anesthetics is unpleasant and can irritate the patient's airway while a patient is awake.

Thus, a number of benefits may be realized from stable liquid formulations of volatile gas anesthetics including but not limited to eliminating the need for inhalation of volatile gas anesthetics via the patient's airway, as well as rendering the administration of numerous agents in order to induce and/or maintain a desired state of anesthesia in a patient unnecessary.

One method of preparation of stable liquid formulations of volatile gas anesthetics in fluoropolymer-based emulsions is disclosed in U.S. Patent Application Publication No. 2008/0234389, FLUOROPOLYMER-BASED EMULSIONS FOR THE INTRAVENOUS DELIVERY OF FLUORINATED VOLATILE ANESTHETICS by Mecozzi et al. Specifically, Mecozzi et al. discloses emulsions and nanoemulsions of perfluorinated and/or perhalogenated volatile anesthetics, for intravenous delivery to a patient to induce and maintain anesthesia in a patient. (Mecozzi et al., paragraph [0012]). To accomplish the same, Mecozzi et al. discloses that "the present formulations comprise a combination of a surfactant, such as one or more semi-fluorinated block copolymers, and a stabilizing additive, such as one or more perhalogenated fluorocarbons, capable of generating an emulsion of a large amount of a fluorinated volatile anesthetic dispersed in an aqueous solution." (Mecozzi et al., paragraph [0013]). Mecozzi et al. further state that "the present therapeutic formulations provide enhanced delivery performance relative to conventional lipid-base delivery systems by enabling emulsions having higher concentrations of fluorinated volatile anesthetics." (Mecozzi et al., paragraph [0014]). Further, with respect to the formulations akin to at least some embodiments of the present invention, Mecozzi et al. state that "combinations of simple lipids such as soy bean oil and glycerol (Intralipid) could be used for making anesthetic emulsions. While these results demonstrate the potential feasibility of lipid emulsions for the delivery of volatile anesthetics, there are significant drawbacks to this approach which hinder its practical implementation. First, emulsions of volatile fluorinated anesthetics based on Intralipid are not expected to be stable over time at high anesthetic concentrations. The effectiveness of these formulations for intravenous administration of volatile anesthetics, therefore, is expected to degrade significantly as a function of time. This property is undesirable as it renders such lipid-based formulations short practical lifetimes and shelf lives. Second, common lipids such as Intralipid have been shown to emulsify a maximum of 3.6% in volume of sevoflurane. This substantial limitation on the volume of anesthetic capable of emulsification is expected to present a significant challenge for practical implementation of lipid-based delivery systems for intravenously administered fluorinated volatile anesthetics." (Mecozzi et al., paragraph [0009]).

It was subsequently determined, however, that a fluoropolymer-based sevoflurane emulsion, such as is disclosed by Mecozzi et al., produced an unexpected allergic-type clinical reaction in canines (Johnson et al., 2011). In an abstract co-authored by Mecozzi, it states that although the fluorocarbon-based sevoflurane emulsion produced general anesthesia in dogs, the dogs also experienced hypotension and clinical signs of an allergic-like response, i.e., vasodilation, urticaria, and pruritus upon recovery (Johnson et al., 2011). It was further determined that emulsions lacking sevoflurane, while failing to induce anesthesia, still elicited the allergic response (Johnson et al., 2011). The conclusion of the study was that an allergic response leading to histamine release, likely initiated by the fluorocarbon-based polymer F13M5 of the emulsion associated with intravenous fluorocarbon-based emulsion of sevoflurane, via an immunoglobulin pathway, and therefore, the usefulness of the formulation was deemed limited (Johnson et al., 2011). It is believed that the incorporation of a perfluorinated stabilizing additive in combination with the fluorocarbon-based polymer F13M5, further exacerbated the allergic response observed in the canine subjects.

Thus, it would be highly beneficial to provide stable liquid formulations of volatile gas anesthetic in a medium that does not induce undesirable responses or side effects upon administration of the formulation to a patient.

SUMMARY OF THE INVENTION

In view of the numerous and substantial benefits to be realized from a stable liquid formulation of a volatile gas anesthetic, it is one aspect of the present invention to provide a stable liquid formulation of at least one volatile gas anesthetic in therapeutically effective amounts. It is a further aspect of the present invention to provide a stable liquid nanoemulsion comprising one or more volatile gas anesthetic. At least one embodiment of the present invention provides stable and injectable liquid formulations of one or more volatile gas anesthetic having a concentration sufficient to induce and maintain anesthesia and/or general anesthesia in a patient.

In one embodiment, the volatile gas anesthetic comprises a halogenated ether. In another embodiment, the volatile gas anesthetic is isoflurane. In yet another embodiment, the volatile gas anesthetic is sevoflurane. In yet one further embodiment, the volatile gas anesthetic is desflurane. In further embodiments, other less known volatile gas anesthetics may be used.

In another aspect, the stable liquid formulations of a volatile gas anesthetic comprise at least one surfactant. In one embodiment of the present invention, the surfactant comprises a poloxamer. In one further embodiment, the poloxamer comprises a block polymer. In yet one further embodiment, the block polymer comprises a central hydrophobic block, and yet another embodiment comprises a hydrophilic block attached at opposite ends of the hydrophobic block. In at least one embodiment, the stable liquid formulations of a volatile gas anesthetic comprise a poloxamer having a central, hydrophobic block comprising a polypropylene oxide attached between two hydrophilic blocks of polyethylene oxide.

A further aspect of the stable liquid formulation of the present invention further comprises a plurality of surfactants. In at least one embodiment, the stable liquid formulations of a volatile gas anesthetic comprise at least one surfactant consisting of an ethylene oxide/polypropylene oxide block copolymer.

The present invention further envisions stable liquid formulations of a volatile gas anesthetic comprising a buffer solution. In at least one embodiment, the buffer solution comprises a phosphate buffer solution ("PBS"). In one other embodiment, the buffer solution comprises a Hank's balanced salt solution ("HBSS"), and in yet one further embodiment, the buffer solution comprises HBSS without calcium or magnesium.

It is another aspect of the present invention to provide stable liquid formulations of a volatile gas anesthetic in solution with a lipid. In one embodiment, the stable liquid formulation of a volatile gas anesthetic is in solution with a plurality of lipids. Yet another embodiment of a stable liquid formulation of a volatile gas anesthetic comprises a solution having an amount of INTRALIPID® (Baxter Healthcare Corporation, Deerfield, Ill.).

Another aspect of the present stable liquid formulations of a volatile gas anesthetic is that administration via injection, such as, for example, intravenously, will accelerate the distribution of the volatile gas anesthetic to the tissues of the body, including the brain, thereby reducing the time of induction of general anesthesia or sedation. Further, intravenous injection of a stable liquid formulation of a volatile gas anesthetic will eliminate the need for the use of intravenous induction agents to induce unconsciousness and amnesia, i.e., general anesthesia.

Yet another aspect of the present invention is to provide for intravenous injection of a stable liquid formulation of a volatile gas anesthetic so as to greatly improve the margin of safety in the induction and maintenance of anesthesia and/or general anesthesia. More in particular, volatile gas anesthetics, particularly intravenously administered volatile anesthetics, are safer for hemodynamically compromised patients than conventional intravenous induction agents, such as those mentioned above (Lucchinetti et al., 2008). As one example, tissue and/or plasma concentrations of volatile gas anesthetics can be measured continuously in real time using existing portable infrared exhaled gas analyzers, thereby allowing more precise titration and superior control over the depth of sedation or general anesthesia or during the administration/dosification for therapeutic, hypothermia, and/or other treatment protocols. This simply is not possible with other intravenous induction agents, such as those listed above, given the fact that those agents are excreted from the body via slow hepatic metabolism, as opposed to the rapid elimination of volatile gas anesthetics through the lungs, with minimal hepatic metabolism.

In one further embodiment, the stable liquid formulations of a volatile gas anesthetic of the present invention allow for the elimination of inhalation as a means of delivery. As a result, the present invention also eliminates the need for the highly specialized and expensive vaporizers and the network of copper piping required for volatile gas anesthetics to be mixed with other gases and delivered to the patient as a vapor for inhalation, as well as eliminating the need for the highly specialized training of personnel to operate the same. Moreover, stable liquid formulations of a volatile gas anesthetic will permit downsizing of present bulky and expensive anesthesia delivery systems. A further benefit of simplifying the means of administration is to enable a greater number of providers to administer anesthetics both inside and outside of the operating room including, but not limited to, in the field, ambulance, emergency room, office, battlefield, inner and outer space, etc., thereby increasing the availability of anesthesia where previously impracticable or impossible. Moreover, elimination of the bulky, expensive, and specialized components of present anesthesia delivery systems, along with the specialized training required to operate such systems, will markedly reduce the overall cost of general anesthesia, while at the same time, providing greater efficiency and safety in the performance of surgical or diagnostic procedures requiring sedation/anesthesia. This will translate into cost savings throughout the entire medical profession.

Thus, stable and injectable liquid formulations of volatile gas anesthetics approach the physical and biological characteristics of an ideal anesthetic by producing a more stable physiologic state during general anesthesia, providing the ability of inducing the continuum of sedation, moderate or deep sedation, or general anesthesia with one composition, while simplifying the equipment and training required to administer volatile gas anesthetics.

In yet another aspect of the present invention, stable and injectable liquid formulations of a volatile gas anesthetic are administered to patients experiencing acute ischemic or inflammatory events including, but not limited to, cardiac arrest, stroke, myocardial infarction, traumatic brain injury or spinal cord injury, or refractory seizures, i.e., status epilepticus, or as cellular, tissue or organ preservation agents, either alone or in combination with other pre-existing or novel organ preservation agents or solutions. In another aspect, the stable and injectable liquid formulations of a volatile gas anesthetic are utilized to induce hypothermia without the need for sophisticated and costly blood, body or head/brain cooling devices. There is evidence that volatile gas anesthetics, whether inhaled or injected, will induce poikilothermia, i.e., loss of thermostatic control of body temperature, in patients receiving general inhalational anesthesia, resulting in hypothermia, unless patients are actively warmed (Waltman et al., 1955; MacKenzie, 1996). Hypothermia, by itself, has proven potential to protect brain and heart tissue against ischemia-reperfusion injury, and is currently approved for use in cardiac arrest of any cause by the American Heart Association (AHA) guidelines for CPR for brain protection/resuscitation (Field et al., 2010). Hypothermia is also beneficial in patients experiencing spinal cord injury for the same reasons, i.e., spinal cord protection/preservation (Martinez-Arizala et al., 1992). Thus, stable injectable formulations of a volatile gas anesthetic alone or as an adjunct will facilitate the wider therapeutic application of mild to moderate therapeutic hypothermia (34° C. to 36° C.), after cardiac arrest, traumatic brain and/or spinal cord injury, and in the future, may facilitate protocols designed to induce protection after massive traumatic injury in the battlefield by inducing states of "therapeutic suspended animation" for delayed resuscitation, or "induced hibernation" for brain protection.

Thus, another significant benefit of a stable injectable liquid formulation of a volatile gas anesthetic of the present invention is that it can induce hypothermia without the need for sophisticated, specialized, and expensive blood, body or head/brain cooling devices, as are presently required by some treatment protocols. Furthermore, stable injectable liquid formulations of a volatile gas anesthetic may act synergistically with hypothermia to enhance protection of tissues against ischemia-hypoxia-reperfusion injury, with the added benefit of allowing safe administration at an earlier period of time following these insults, i.e., the scene of an accident, a battlefield, etc., thus maximizing the therapeutic potential of hypothermia and volatile gas anesthetic induced cytoprotection.

In one further aspect of the present invention, stable and injectable liquid formulations of a volatile gas anesthetic are administered to patients as a cytoprotective agent for therapeutic applications and/or for the purpose of organ and cell preservation for use in cell, organ, tissue, or stem cell transplantation. More in particular, it has demonstrated that volatile gas anesthetics, whether inhaled or injected, have cytoprotective, anti-apoptotic properties against cellular ischemia-reperfusion injury at therapeutically effective dosages, through a mechanism of anesthesia preconditioning, similar to ischemic preconditioning of tissues (Lange et al., 2006; Wang et al., 2008). In addition, it has also been demonstrated that volatile gas anesthetics have anti-inflammatory and anti-convulsive properties (Delgado-Escueta et al., 1982; Li et al., 2009). Therefore, stable injectable liquid formulations of a volatile gas anesthetic will have the added benefit of facilitating novel therapeutic applications in patients, such as, to induce poikilothermia and/or to serve as a cytoprotective agent, wherever and whenever applicable, by specially trained anesthesiologists and anesthetists, as well as by generally trained medical personnel, in hospital and/or non-hospital settings.

The present invention further envisions methods of preparing various stable liquid formulations of volatile gas anesthetics, in accordance with at least the methods and procedures disclosed below. It is a further aspect of the present invention to provide a reliable method to analyze stable liquid formulations of volatile gas anesthetics to accurately determine the actual concentration of volatile gas anesthetic(s) present in a stable liquid formulation, once again, as disclosed in detail below.

A further aspect of the present invention comprises a kit for the storage, transportation, and administration of stable formulations of a volatile gas anesthetic. In at least one embodiment, the present stable liquid formulations of volatile gas anesthetics will be manufactured, packaged, labeled and distributed in glass, light resistant, e.g., amber, waterproof and airtight, "ready-use" cartridges, syringes or bottles, to be kept refrigerated during storage. The packaging itself, i.e., the airtight sealed cartridge, syringe or bottle made of glass or other such suitable material, may be labeled and pre-calibrated for titrated rates of infusion. The volume of each container is determined via in vivo studies to calibrate the volume necessary for induction and maintenance of anesthesia by infusion with the present stable liquid formulations of a volatile gas anesthetic. The container itself can serve as a cartridge for direct placement into a preselected infusion pump, similar to a syringe pump, however, having a larger capacity, such as, by way of example, capacity to receive a 50 cc to 100 cc syringe or ampule. The unique feature of such an infusion pump is that it will accept larger volumes of injectable anesthetic glass cartridges without modification, and without having to expose the stable liquid formulation of a volatile gas anesthetic to ambient air. After engagement of the cartridge containing the present stable liquid formulation of a volatile gas anesthetic into the infusion pump, the sealed nipple or TEFLON® stopper of the glass syringe or bottle will be punctured, in the same way as is done with intravenous bags or bottles. Once punctured, the stable liquid formulation of a volatile gas anesthetic will be ready for infusion directly into a patient's intravenous line, thus allowing ease of use by the operator and achievement of rates of infusion to produce a reliable range of levels of sedation/general anesthesia, or the administration of a predetermined bolus dose, or for use as therapeutic agent, as described above, all without exposing the stable liquid formulation of a volatile gas anesthetic to ambient air.

Once used, a spent cartridge can be easily interchanged with a new cartridge containing the stable liquid formulation of a volatile gas anesthetic, allowing for uninterrupted continuous infusion. Insertion of an airtight glass syringe or bottle will not require needle aspiration of the solution into another syringe or container, nor exposure of the present stable liquid formulation of a volatile gas anesthetic to ambient air at any time during its preparation and administration, as is currently done for other intravenous agents, thereby preventing degradation or contamination either prior to or while administering the same to a patient.

The present stable liquid formulations of a volatile gas anesthetic can be marketed alone or as a component of an entirely novel anesthesia delivery system, such as described above, complete with portable workstation. Thus, the present, bulky and expensive anesthesia delivery equipment can be replaced with a greatly scaled down anesthesia workstation. The key features of this new sedation/anesthesia delivery system are its portability and self-containment and will include one or more of the following: the present stable liquid formulations of a volatile gas anesthetic in a glass syringe cartridge, and an infusion pump that can be attached to an IV pole; a portable ventilator with breathing circuit and an $O_2$/air/gas mixture; a portable exhaled gas monitor, to measure $CO_2$, $O_2$ and volatile gas anesthetic concentrations. This system can be used in conjunction with pre-existing monitors including, but not limited to, pulse oximetry, EKG monitoring, etc.

The methods, compositions and kits herein described can be used in connection with pharmaceutical, medical, and veterinary applications, as well as fundamental scientific research and methodologies, as would be identifiable by a skilled person upon reading of the present disclosure. These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which:

FIG. 2Av2 is an alternate graphical representation of isoflurane concentration versus time as presented in FIG. 2A in a 4.5% isoflurane/INTRALIPID® based nanoemulsion prepared in accordance with an embodiment of the present invention and stored in a closed container at a temperature of about 4° Celsius as measured by HPLC.

FIG. 4A is yet another graphical representation of nanoparticle size distribution versus time in a 4.5% isoflurane/INTRALIPID® based nanoemulsion prepared in accordance with an embodiment of the present invention and stored in a closed container at a temperature of about 4° Celsius as measured by direct light scattering.

FIG. 8 is a graphical representation of known isoflurane concentrations versus weight of isoflurane emulsions.

FIG. 9 is a graphical representation of calculated isoflurane concentrations from standard curve versus expected isoflurane concentration.

FIG. 10 is a graphical representation of known isoflurane concentrations versus area under curve of isoflurane peak as measured by HPLC.

FIG. 11 is a graphical representation of isoflurane concentration versus time (hours) in pure isoflurane and a 4.5% isoflurane/INTRALIPID® based nanoemulsion prepared in accordance with an embodiment of the present invention and stored in an open container at a room temperature of about 21° Celsius as measured by weight.

FIG. 12 is a graphical representation of isoflurane concentration versus time in a 4.5% isoflurane/INTRALIPID® based nanoemulsion prepared in accordance with an embodiment of the present invention and stored in an open container at a room temperature of about 21° Celsius as measured by weight.

FIG. 13 is a graphical representation of isoflurane concentration versus time in a 4.5% isoflurane/INTRALIPID® based nanoemulsion prepared in accordance with an embodiment of the present invention and stored in a closed container at a temperature of about 4° Celsius as measured by weight.

FIG. 14 is a graphical representation of the gradual decrease in the height of peak of isoflurane with decreasing known concentration of isoflurane in emulsion as measured by FTIR.

FIG. 15 is a graphical representation of the gradual decrease in the height of peak of isoflurane with decreasing known concentration of isoflurane in emulsion as measured by FTIR.

FIG. 16 is a graphical representation of known isoflurane concentrations versus area under curve of isoflurane peak as measured by ATR-FTIR (1300-1260 $cm^{-1}$).

FIG. 17 is a graphical representation of known isoflurane concentrations versus area under curve of isoflurane peak as measured by ATR-FTIR (1225-1011 $cm^{-1}$).

FIG. 18 is a graphical representation of calculated isoflurane concentrations from standard curve versus expected isoflurane concentration as measured by ATR-FTIR (1300-1260 $cm^{-1}$).

FIG. 19 is a graphical representation of calculated isoflurane concentrations from standard curve versus expected isoflurane concentration as measured by ATR-FTIR (1225-1011 $cm^{-1}$).

FIG. 20 is a graphical representation of modeled versus measured isoflurane loss over time as measured by ATR-FTIR (1300-1260 $cm^{-1}$).

FIG. 20A is a graphical representation of isoflurane concentration (radiofrequency unit) versus time as measured by ATR-FTIR (1300-1260 $cm^{-1}$) for both 20% and 10% isoflurane/non-lipid based nanoemulsions prepared in accordance with an embodiment of the present invention and stored in an open container at a room temperature of about 25° Celsius.

FIG. 21A is a graphical representation of the percentage of rats who anesthetized ($ED_{50}$) following administration of an injection of a 4.5% isoflurane/INTRALIPID® based nanoemulsion prepared in accordance with an embodiment of the present invention.

FIG. 21B is a graphical representation of the percentage of rats who died after respiratory arrest ($LD_{50}$) following administration of an injection of a 4.5% isoflurane/INTRALIPID® based nanoemulsion prepared in accordance with an embodiment of the present invention.

FIG. 22 is a graphical representation of the time of loss of consciousness, loss of forepaw reflex, loss of response to tail vain clamp, and corneal reflex of male Lewis rats immediately preceding and following administration of an injection of a 4.5% isoflurane/INTRALIPID® based nanoemulsion prepared in accordance with an embodiment of the present invention.

FIG. 23 is a tabulated representation of the time to and duration of induction of anesthesia and the time of recovery of consciousness, forepaw reflex, response to tail vein clamp and corneal reflex of male Lewis rats immediately preceding and following administration of an injection of a 4.5% isoflurane/INTRALIPID® based nanoemulsion prepared in accordance with an embodiment of the present invention.

FIG. 24 is a tabulated representation of the histology of the brain, heart, lung, liver and kidney of male Lewis rats following administration of an injection of a 4.5% isoflurane/INTRALIPID® based nanoemulsion prepared in accordance with an embodiment of the present invention.

FIG. 25 is a tabulated representation of biochemical markers detected in male Lewis rats following administration of an injection of a 4.5% isoflurane/INTRALIPID® based nanoemulsion prepared in accordance with an embodiment of the present invention.

FIG. 26 is a graphical representation of an experimental design to evaluate the cytoprotective effects of isoflurane against oxidative stress induced apoptosis.

FIG. 27 is a graphical representation of the cytoprotective effects of isoflurane against oxidative stress induced apoptosis.

FIG. 28 is a graphical representation of the protein kinase (p38 MAPK) activity cytoprotective effects of isoflurane against oxidative stress induced apoptosis.

DETAILED DESCRIPTION OF THE PREFERRED EMBODIMENT

Figure 1A:
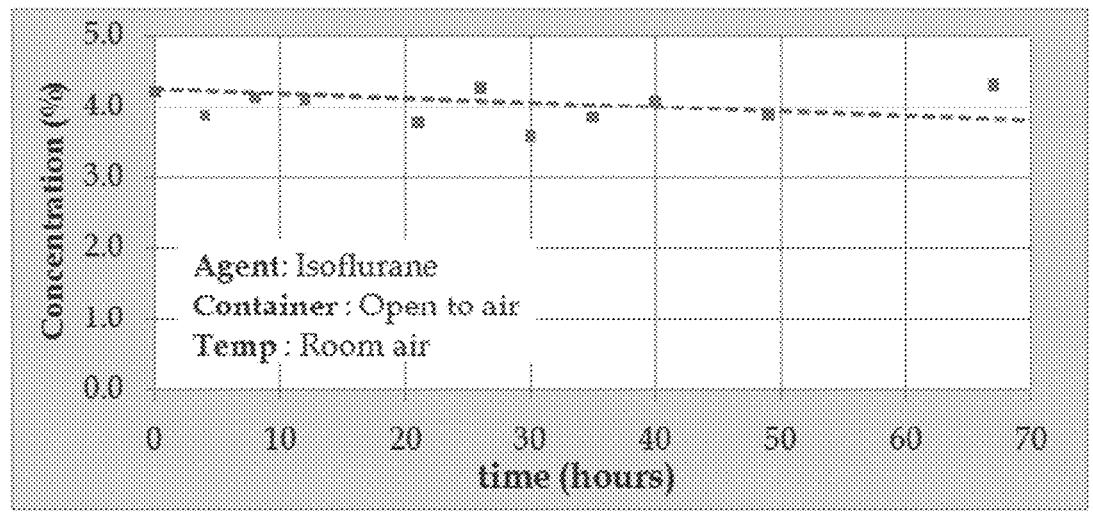
FIG. 1A is a graphical representation of isoflurane concentration versus time in a 4.5% isoflurane/INTRALIPID® based nanoemulsion prepared in accordance with an embodiment of the present invention and stored in an open container at a room temperature of about 25° Celsius as measured by HPLC.

The present invention is directed to stable liquid formulations of volatile gas anesthetics, as well as methods of preparation, methods of testing, and methods of treatment utilizing the same, and kits useful in the storage, transport, and administration of stable liquid formulations of volatile gas anesthetics.

Several aspects of the invention are described below, with reference to examples for illustrative purposes only. It should be understood that numerous specific details, relationships, and methods are set forth to provide a full understanding of the invention. One having ordinary skill in the relevant art, however, will readily recognize that the invention can be practiced without one or more of the specific details or practiced with other methods, protocols, reagents, and animals. The present invention is not limited by the illustrated ordering of acts or events, as some acts may occur in different orders and/or concurrently with other acts or events. Many of the techniques and procedures described, or referenced herein, are well understood and commonly employed using conventional methodology by those skilled in the art.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. It will be further understood that terms, such as those defined in commonly used dictionaries, should be interpreted as having a meaning that is consistent with their meaning in the context of the relevant art and/or as otherwise defined herein.

The terminology used herein is for the purpose of describing particular embodiments only and is not intended to be limiting of the invention. As used herein, the indefinite articles "a", "an" and "the" should be understood to include plural reference unless the context clearly indicates otherwise. Further, the singular shall include the plural and the plural shall include the singular, unless specifically stated otherwise.

The phrase "and/or", as used herein, should be understood to mean "either or both" of the elements so conjoined, i.e., elements that are conjunctively present in some cases and disjunctively present in other cases.

As used herein, "or" shall have the same meaning as "and/or" as defined above. For example, when separating a listing of items, "and/or" or "or" shall be interpreted as being inclusive, i.e., the inclusion of at least one, but also including more than one, of a number of items, and, optionally, additional unlisted items. Only terms clearly indicated to the contrary, such as "only one of" or "exactly one of", or, when used in the claims, "consisting of", will refer to the inclusion of exactly one element of a number or list of elements. In general, the term "or" as used herein shall only be interpreted as indicating exclusive alternatives (i.e., "one or the other but not both") when preceded by terms of exclusivity, such as "either", "one of", "only one of", or "exactly one of."

As used herein, the terms "including", "includes", "having", "has", "with", or variants thereof, are intended to be inclusive similar to the term "comprising."

The terms "anesthetic" and "anesthetic agent" as used herein shall mean any drug or agent that is capable of producing a complete or partial loss of feeling in a patient, i.e., capable of producing a state of anesthesia.

The phrase "block polymer" as used herein refers to synthetic polymers comprising alternating sections of one chemical composition separated by sections of a different chemical nature, or by a coupling group having a low molecular weight. As one example, a block polymer may comprise a poloxamer having a hydrophobic central polymer and a hydrophilic polymer on either end. As another example, a block polymer may comprise an ethylene oxide/propylene oxide block copolymer.

The term "buffer" as used herein refers to a solution containing both a weak acid and its conjugate weak base, wherein the pH of the buffer solution changes only slightly upon addition of an acid or base. Examples of buffer solutions referenced herein include a phosphate buffer solution, or "PBS", and Hank's balanced salt solution, or "HBSS."

"Formulation" as used herein shall mean and include any collection of components of a compound, mixture, or solution selected to provide optimal properties for a specified end use, including product specifications and/or service conditions. The term "formulation" shall include colloidal solutions, dispersions, emulsions, microemulsions, and nanoemulsions, including oil-in-water emulsions and water-in-oil emulsions, and suspensions.

The term "hydrophilic" refers to compounds having a strong affinity for water, tending to bind to or absorb water molecules.

The term "hydrophobic" refers to compounds which are generally incapable of dissolution in water such as is characteristic of oils, fats, waxes, etc.

The term "lipid" as used herein refers to fats and fat-derived materials, and includes all substances which are relatively insoluble in water but soluble in organic solvents, related either actually or potentially to fatty acid esters, fatty alcohols, sterols, waxes, etc., and are utilizable by living animal organisms.

The term "phospholipid" as used herein refers to a group of lipid compounds widely found in nature that hydrolyze into phosphoric acid, an alcohol, a fatty acid, and a nitrogenous base, and includes such substances as lecithin, cephalin, and sphingomyelin.

As used herein, the term "surfactant" shall include and refer to any compound that reduces surface tension when dissolved in water or aqueous solutions, or which reduces surface tension between two liquids, or between a liquid and a solid. Surfactants include detergents, wetting agents, and emulsifiers, which each operate via similar chemical mechanisms, but differ in nature by the surfaces which they affect. "Surfactant" and "surface active agent" may be used interchangeable herein in reference to any such compound.

The term "perfluorinated" as used herein refers to a fluorocarbon compound in which each hydrogen atom directly attached to a carbon atom in the underlying hydrocarbon is replaced by fluorine.

As used herein, "emulsifier" shall refer to a surface active agent, or surfactant, comprising either proteins or carbohydrate polymers which act by coating the surfaces of a dispersed fat or oil particle, thus preventing the particles from coalescing, known as protective emulsifiers; or, long-chain alcohols and fatty acids which reduce the surface tension at the interface of suspended particles due to the solubility of the emulsifier itself, as in soaps and detergents.

The term "emulsion" as used herein refers to a stable mixture of two or more immiscible liquids held in suspension by a small amount of surface active agents, such as an emulsifier. Emulsions comprise a continuous phase and a dispersed phase, for example, an oil-in-water emulsion comprises oil droplets dispersed in a continuous aqueous phase, wherein a water-in-oil emulsion comprises amounts of water dispersed in a continuous oily phase.

A "nanoemulsion" as used herein refers to an emulsion composed of nanoscale droplets of an immiscible liquid dispersed within another.

The term "nanoparticle" as used herein refers to any particle that is measured on a "nano" scale (i.e., nanometer). In some embodiments, a nanoparticle is a particle ranging in size from about 1 nm to about 100 nm. In other embodiments, a nanoparticle is a particle that is less than about 200 nm.

The phrase "nanoparticle size distribution" as used herein refers to a range of values or a graphical representation of values that defines the relative size or amounts of nanoparticles present. In at least one embodiment, a nanoparticle size distribution refers to such values relative to a given point in time.

The term "stable" as used herein refers to any chemical compound, mixture, or solution which tends to maintain its form, phase, state, and chemical properties and composition without external forces or additives, and shall include thermodynamic stability, and may be exhibited and measured such as via particle size and particle size distribution and/or concentration of one or more volatile components of a compound, mixture, or solution.

As used herein, "volatile gas anesthetic" refers to any drug or agent capable of inducing and/or maintaining a state of general anesthesia upon administration to a patient, wherein the drug or agent is in a liquid state at the standard temperature and pressure but requires vaporization into gas at which administration via inhalation to a patient would normally occur.

As used herein, the term "patient" refers to any animal (e.g., mammals, birds, reptiles, amphibians, fish), including, but not limited to, humans, non-human primates, rodents, and the like, which is to be the recipient of a particular treatment. Typically, the terms "patient" and "subject" may be used interchangeably herein in reference to a patient.

As used herein, the terms "administer" and "administering" refer to providing a therapeutically effective amount of a chemical or biological compound or pharmaceutical composition to a patient, using subcutaneous, transcutaneous, intracutaneous, intravenous, intraarterial, intramuscular, intradermal, intracranial, and the like administration. The chemical formulations of the present invention can be administered alone, but may be administered with other compounds, excipients, fillers, binders, carriers or other vehicles selected based upon the chosen route of administration and standard pharmaceutical practice. Administration may be by way of carriers or vehicles, such as injectable solutions, including sterile aqueous or non-aqueous solutions, or saline solutions; suspensions, emulsions, microemulsions, or nanoemulsions; micelles; synthetic polymers; microspheres; nanoparticles; and the like.

The chemical compound or pharmaceutical composition of the present invention, i.e., stable liquid formulations of one or more volatile gas anesthetic, may also be included, or packaged, with other non-toxic compounds, such as pharmaceutically acceptable carriers, excipients, binders and fillers including, but not limited to, glucose, lactose, gum acacia, gelatin, mannitol, xanthan gum, locust bean gum, galactose, oligosaccharides and/or polysaccharides, starch paste, magnesium trisilicate, talc, corn starch, starch fragments, keratin, colloidal silica, potato starch, urea, dextrans, dextrins, and the like. Specifically, the pharmaceutically acceptable carriers, excipients, binders, and fillers contemplated for use in the practice of the present invention are those which render the compounds of the invention amenable to intravenous delivery, subcutaneous delivery, transcutaneous delivery, intracutaneous delivery, intravenous, intraarterial delivery, intramuscular delivery, intradermal delivery, intracranial delivery, and the like. Moreover, the packaging material may be biologically inert or lack bioactivity, such as plastic polymers, silicone, etc., and may be processed internally by the subject without affecting the effectiveness of the volatile gas anesthetic packaged and/or delivered therewith.

A "bolus dose" as used herein shall refer to the rapid administration of a relatively large dosage of a stable liquid formulation of a volatile gas anesthetic via intravenous injection in order to decrease the response time of a patient to the same.

The phrase "therapeutically effective amount" as applied to the stable liquid formulations of volatile gas anesthetics described herein, means the amount of a stable liquid formulation of a volatile gas anesthetic necessary to render the desired therapeutic result. For example, a therapeutically effective amount is an amount of a stable liquid formulation of a volatile gas anesthetic required to induce or maintain a state of anesthesia or general anesthesia, to induce poikilothermia and/or hypothermia, to treat, cure, or alleviate the symptoms of a disorder for which the formulation is being administered, and/or to trigger cytoprotective properties for the purpose of organ and cell preservation. Amounts effective for the particular therapeutic goal sought will depend upon a variety of factors including the disorder being treated and its severity and/or stage of development/progression; the bioavailability, and activity of the specific compound or formulation used; the route or method of administration and introduction site on the subject; the rate of clearance of the specific compound or biologic and other pharmacokinetic properties; the duration of treatment; inoculation regimen; drugs used in combination or coincident with the specific compound, biologic or composition; the age, body weight, sex, diet, physiology and general health of the subject being treated; and like factors well known to one of skill in the relevant scientific art. Some variation in dosage will necessarily occur depending upon the condition of the patient being treated, and the physician or other individual administering treatment will, in any event, determine the appropriate dose for an individual patient.

As used herein, "disorder" refers to a disorder, disease or condition, or other departure from healthy or normal biological activity, and the terms can be used interchangeably. The terms refer to any condition that impairs normal function. The condition may be caused by sporadic or heritable genetic abnormalities. The condition may also be caused by nongenetic abnormalities. The condition may also be caused by injuries to a subject from environmental factors, such as, but not limited to, cutting, crushing, burning, piercing, stretching, shearing, injecting, or otherwise modifying a subject's cell(s), tissue(s), organ(s), system(s), or the like.

As used herein, "treatment" or "treating" refers to arresting or inhibiting, or attempting to arrest or inhibit, the development or progression of a disorder and/or causing, or attempting to cause, the reduction, suppression, regression, or remission of a disorder and/or a symptom thereof. As would be understood by those skilled in the art, various clinical and scientific methodologies and assays may be used to assess the development or progression of a disorder, and similarly, various clinical and scientific methodologies and assays may be used to assess the reduction, regression, or remission of a disorder or its symptoms. "Treatment" or "treating" as used herein shall also refer to various therapeutic treatments including anesthesia, general anesthesia, cytoprotection, and poikilothermia or therapeutic hypothermia.

The term "anesthesia" as used herein refers to the absence of all sensation, especially sensitivity to pain, induced by an anesthetic substance or traumatic or pathophysiologic damage to nerve tissue, or hypnosis. Anesthesia induced for medical or surgical purposes may be topical, local, regional, or general.

The phrase "general anesthesia" as used herein refers to the absence of sensation and consciousness as induced by various anesthetic agents given by inhalation or intravenous injection. The components of general anesthesia are analgesia, amnesia, muscle relaxation, control of vital signs, and unconsciousness. The depth of anesthesia is planned to allow a surgical procedure to be performed without the patient experiencing pain, moving, or having any recollection of the procedure being performed. General anesthesia may only be administered by an anesthesiologist, anesthesia assistant, or a Certified Registered Nurse Anesthetist.

As used herein, the term "cytoprotection" refers to preventing, halting, inhibiting, or slowing deterioration, cell cycle abnormality, damage or death of a cell or a population of cells. Such deterioration, cell cycle abnormality, damage or death may be elicited, or at least partially elicited, by one or more external factors or by one or more intrinsic factors, including apoptotic or ischemic, cell cycle and necrotic or necro-apoptotic factors, or by a combination of such external and intrinsic factors. A population of cells includes cell cultures, tissues, organs and organ systems.

The phrase "cytoprotective agent" as used herein refers to one or more agents, including but not limited to chemical compounds, pharmaceuticals and/or formulations that provide protection against injury, i.e., cytoprotection, to a cell or population of cells, including cell cultures, tissues, organs and organ systems.

The term "hypothermia" as used herein refers to a condition wherein a patient's body temperature is reduced several degrees below normal, which for human patients is below 98.6° F. or 37° C., and may be caused by prolonged exposure to cold and/or damp conditions. Therapeutic hypothermia as used herein also includes the deliberate and controlled reduction of body temperature of a patient, such as, for example, for purposes of preparing the patient for certain surgical procedures, or to protect or recover tissues against or from injury.

As used herein, "poikilothermia" refers to the inability to regulate core body temperature. Such conditions are observed especially in patients with some spinal cord injuries and in patients under general anesthesia.

As previously described, stable and injectable liquid formulations of a volatile gas anesthetic provide a more complete and stable state of anesthesia characterized by more rapid onset or induction, faster emergence, i.e., a shorter half life, and more hemodynamic stability than the inhaled form, while retaining the ability to continuously monitor breath-to-breath expired gas concentration. Thus, the present inventive formulations allow inducement and maintenance of anesthesia and/or general anesthesia using a single agent with the added benefit of the ability to administer the volatile gas anesthetic independent of the bulky and costly anesthesia equipment required by existing inhalational anesthesia delivery methods. Thus, the stable and injectable liquid formulations of a volatile gas anesthetic of the present invention revolutionize the delivery of general anesthesia.

More in particular, the stable liquid formulations of volatile gas anesthetics of the present invention not only provide the convenience and ease of use including, but not limited to, intravenous infusion, which is among the main advantage of conventional intravenous induction/anesthetic agents such as propofol, ketamine, thiopental, dexmedetodomine, and etomidate, but further assures greater hemodynamic stability. Specifically, unlike other intravenous anesthetics, the stable liquid formulations of volatile gas anesthetics of the present invention permit monitoring and titration of precise concentrations of the volatile gas anesthetic on a breath-to-breath basis, which is not possible now nor foreseeable in the near future with any other type of intravenous anesthetic agent. The unique and unexpected shelf-life stability of the present stable liquid formulations of volatile gas anesthetics is a further and major advantage over previously described emulsions of volatile liquid anesthetics and will translate into clinically-viable and injectable formulations that will result in enhanced safety in the administration of general anesthesia.

In one aspect, the present invention comprises a stable liquid formulation of a volatile gas anesthetic including at least one volatile gas anesthetic, at least one surface active agent, and a stabilizing agent. The volatile gas anesthetics which may be incorporated into the present formulation include, but are in no manner limited to, isoflurane, sevoflurane, and desflurane. In one embodiment, the stable liquid formulation comprises an amount of a volatile gas anesthetic in the range of between about 1% and 30% by volume. In one further embodiment, the present formulation comprises a volatile gas anesthetic in an amount of about 4.5% by volume, and in yet another embodiment the formulation comprises an amount of volatile gas anesthetic of about 10.0% by volume. It is a further aspect of the present invention to provide a stable liquid formulation which comprises a therapeutically effective amount of a volatile gas anesthetic.

In at least one embodiment, the stable liquid formulation of the present invention comprises an amount of at least one surface active agent. As noted above, surface active agents reduce surface tension between two liquids, such as, a fluorinated anesthetic and an aqueous buffer solution, to prevent, or at least minimize, the coalescence of the liquids into immiscible phases, i.e., phase separation. In one embodiment, the stable liquid formulation of volatile gas anesthetics of the present invention comprises an amount of at least one surface active agent in the range of between about 1% and 10% by weight. One aspect of the stable liquid formulation of the present invention includes a surface active agent which comprises a poloxamer. In one further embodiment, the surface active agent comprises a block polymer, wherein the block polymer has at least one of a hydrophilic block or a hydrophobic block. In yet another embodiment, the surface active agent includes a block polymer having a hydrophobic block and at least one hydrophilic block, and a further embodiment includes a block polymer having a central hydrophobic block and a hydrophilic block attached at either end. In a further aspect, the at least one surface active agent of the stable liquid formulation comprises an ethylene oxide/propylene oxide block polymer, while another aspect includes a plurality of surface active agents, each comprising a different block polymer, such as, by way of example only, different ethylene oxide/propylene oxide block polymers.

As previously stated, the stable liquid formulation of the present invention comprises a stabilizing agent which, as the name implies, is provided to further stabilize the hydrophobic volatile gas anesthetic agents dispersed in a substantially aqueous liquid formulation, or emulsion. In one aspect, the stabilizing agent comprises a lipid compound, such as, but not limited to, INTRALIPID®. In one further embodiment, the stabilizing agent comprises 30% INTRALIPID®, and more in particular, 30% INTRALIPID® having a specific gravity of 0.91.

Of course, the present invention further envisions stable liquid formulations of volatile gas anesthetics wherein the stabilizing agent comprises a non-lipid compound. Thus, at least one embodiment of the present formulation comprises perfluorotributylamine as a stabilizing agent. Perfluorotributylamine exhibits good gas transfer properties which will facilitate the transfer of the volatile gas anesthetic from a stable liquid emulsion into the patient's bloodstream upon injection of the same into the patient. Further, perfluorotributylamine has a small particle size, i.e., less than 200 nm, which will facilitate the formation of a nanoemulsion in accordance with at least one embodiment of present invention. In at least one embodiment, the stabilizing agent comprises perfluorotributylamine in the form of FLUORINERT™ FC-43.

Another aspect of the stable liquid formulation of the present invention is the incorporation of an amount of a buffer solution. As noted above, the stable liquid formulation is substantially aqueous based, which is a result of the aqueous buffer solution. In at least one embodiment, the buffer solution comprises a standard, sterile phosphate buffer solution. In yet another embodiment, the buffer solution comprises a Hank's balanced salt solution, another aqueous based solution. A further aspect of the present formulation comprises a Hank's balanced salt solution without calcium, or without magnesium, or without either.

Another aspect of the present invention is a method of preparing a stable liquid formulation of a volatile gas anesthetic, such as is disclosed in detail in Example I below. Briefly, the present method includes adding an amount of at least one surface active agent to an amount of a buffer solution and thoroughly mixing these reagents together to form a surfactant solution. An amount of a volatile gas anesthetic and an amount of a stabilizing agent are added to the surfactant solution. In at least one embodiment, the surfactant solution is preheated to about 37° C. prior to the addition of the volatile gas anesthetic and/or the stabilizing agent. The subsequent mixture is then emulsified to form a stable liquid formation, or nanoemulsion, comprising the volatile gas anesthetic. In one embodiment, a water bath sonicator is utilized to carry out the emulsification process, as in Examples I-A and I-B below, while in at least one other embodiment, the step of emulsifying the components into a stable nanoemulsion utilizes a high pressure microfluidizer processor, as discussed below in Example I-C.

Yet another aspect of the present invention is a method of treatment with a stable liquid formulation of a volatile gas anesthetic comprising preparing a stable liquid nanoemulsion having at least one volatile gas anesthetic, and administering a therapeutically effective amount of the stable liquid nanoemulsion to a patient. In at least one embodiment, the step of administering the therapeutically effective amount is performed by way of injection including, but not limited to, subcutaneous, transcutaneous, intracutaneous, intravenous, intraarterial, intramuscular, intradermal, or intracranial injection.

Without further elaboration, it is believed that one skilled in the art can, using the preceding description, utilize the present invention to its fullest extent. The following examples are offered by way of illustration, not by way of limitation.

While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification.

All publications and patent documents cited in this application are incorporated by reference in pertinent part for all purposes to the same extent as if each individual publication or patent document were so individually denoted. By citation of various references in this document, Applicant does not admit any particular reference is "prior art" to their invention.

The methods and compositions herein described and the related kits are further illustrated in the following examples, which are provided by way of illustration and are not intended to be limiting. It will be appreciated that variations in proportions and alternatives in elements of the components shown will be apparent to those skilled in the art and are within the scope of embodiments of the present invention. Theoretical aspects are presented with the understanding that Applicant does not seek to be bound by the theory presented.

Example I

Preparation of Stable Liquid Formulations of Volatile Gas Anesthetics

A. Formulation of a 4.5% Isoflurane/INTRALIPID® Based Emulsion.
Reagents.
1. LUTROL® F68NF
   BASF Corp., Florham Park, N.J.
2. 30% INTRALIPID® (specific gravity=0.91)
   Baxter Healthcare, Deerfield, Ill.
3. Phosphate buffer solution ("PBS")
   e.g., Invitrogen Corp., Carlsbad, Calif.
4. Isoflurane (clinical grade)
Equipment.
1. 1 L beaker
2. 500 mL filter flask
3. 50 cc conical tube
4. Ice and bucket
5. Temperature controlled water bath
6. Vortexer
   e.g., Vortex Mixer, VWR Int'l., Radnor, Pa.
7. Water bath sonicator—Model F550 Sonic Dismembrator Fisher Scientific, Springfield, N.J.
Preparation.

A surfactant solution is initially prepared by weighing out 200 grams ("g") of LUTROL® F68NF, a block polymer having a central, hydrophobic block comprising a polypropylene oxide attached between two hydrophilic blocks of polyethylene oxide, and adding the amount of the block polymer to 500 milliliter ("mL") of sterile phosphate buffer solution ("PBS") in a sterile 1 L beaker with a stir bar, and covering the beaker. Initiate mixing at medium speed so as not to cause bubble formation, and continue mixing until all of the surfactant is completely dissolved, which may require mixing overnight. The resultant solution will comprise the surfactant, LUTROL® F68NF, at a final concentration of 0.400 mg/mL in PBS, i.e., a 40% weight/volume surfactant solution. The surfactant concentration assumes that the total weight of surfactant is dissolved in the total volume of PBS, since the surfactant is amphiphilic and soluble in both hydrophilic and hydrophobic solutions. Therefore, 1 g of surfactant dissolved in 50 mL of total solution volume results in a surfactant concentration of 2% weight/volume ("w/v"). The surfactant solution is filtered via a 500 mL sterile filter flask.

A stable liquid emulsion containing 4.5% isoflurane, by volume, is prepared by adding 1.5 mL of a 40% surfactant solution, prepared in accordance with the procedures of the preceding paragraph, and 3.55 mL of PBS in a 50 cc conical glass tube fitted with a TEFLON® stopper. This mixture is heated for 10 minutes in a water bath at a temperature of 37° C. An amount of 0.45 mL liquid isoflurane is added to the heated mixture, the TEFLON® stopper is inserted to seal the conical tube, and the resultant mixture is vortexed for a period of 3 minutes.

Next, an amount of 4.5 mL of 30% INTRALIPID® having a specific gravity of 0.91 is added to the solution after vortexing. The final step in the emulsification process is sonification via a water bath sonicator. The water bath sonicator is programmed for a total sonification time of 3 minutes, pulse on time at 30 seconds, pulse off time at 30 seconds, and amplitude set at 10. The 50 cc conical glass tube fitted with the TEFLON® stopper is carefully placed in the water bath sonicator with care to assure that the bottom of conical tube is not physically contacting the ultrasound crystal. During sonification, the cooling chamber of the water bath sonicator is provided with sufficient ice to maintain a stable temperature in the range of about 6 to 10° C.

After sonification, the TEFLON® stopper of the 50 cc conical glass tube is wrapped with PARAFILM®, to minimize gas transfer.

B. Formulation of a 4.5% Sevoflurane/INTRALIPID® Based Emulsion.
Reagents.
1. LUTROL® F68NF
   BASF Corp., Florham Park, N.J.
2. 30% INTRALIPID® (specific gravity=0.91)
   Baxter Healthcare, Deerfield, Ill.
3. Phosphate buffer solution ("PBS")
   e.g., Invitrogen Corp., Carlsbad, Calif.
4. Sevoflurane (clinical grade)
Equipment.
1. 1 L beaker
2. 500 mL filter flask
3. 50 cc conical tube
4. Ice and bucket
5. Temperature controlled water bath
6. Vortexer
   e.g., Vortex Mixer, VWR Int'l., Radnor, Pa.
7. Water bath sonicator—Model F550 Sonic Dismembrator Fisher Scientific, Springfield, N.J.
Preparation.

A surfactant solution is initially prepared by weighing out 200 g of LUTROL® F68NF, a block polymer having a central, hydrophobic block comprising a polypropylene oxide attached between two hydrophilic blocks of polyethylene oxide, and adding the amount of the block polymer to 500 mL of sterile PBS in a sterile 1 L beaker with a stir bar, and covering the beaker. Initiate mixing at medium speed so as not to cause bubble formation, and continue mixing until all of the surfactant is completely dissolved, which may require mixing overnight. The resultant solution will comprise the surfactant, LUTROL® F68NF, at a final concentration of 0.400 mg/mL in PBS, i.e., a 40% w/v surfactant solution. The surfactant solution is filtered via a 500 mL sterile filter flask.

A stable liquid emulsion containing 4.5% sevoflurane, by volume, is prepared by adding 1.5 mL of a 40% surfactant solution, prepared in accordance with the procedures of the preceding paragraph, and 3.55 mL of PBS solution in a 50 cc conical glass tube fitted with a TEFLON® stopper. This mixture is heated for 10 minutes in a water bath at a temperature of 37° C. An amount of 0.45 mL liquid sevoflurane is added to heated mixture, the TEFLON® stopper is inserted to seal the conical tube, and the resultant mixture is vortexed for a period of 3 minutes.

Next, an amount of 4.5 mL of 30% INTRALIPID® having a specific gravity of 0.91 is added to the solution after vortexing. The final step in the emulsification process is sonification via a water bath sonicator. The water bath sonicator is programmed for a total sonification time of 3 minutes, pulse on time at 30 seconds, pulse off time at 30 seconds, and amplitude set at 10. The 50 cc conical glass tube fitted with the TEFLON® stopper is carefully placed in the water bath sonicator with care to assure that the bottom of conical tube is not physically contacting the ultrasound crystal. During sonification, the cooling chamber of the water bath sonicator is provided with sufficient ice to maintain a stable temperature in the range of about 6 to 10° C.

After sonification, the TEFLON® stopper of the 50 cc conical glass tube is wrapped with PARAFILM®, to minimize gas transfer.

C. Formulation of a 10% Isoflurane/Non-Lipid Based Emulsion.

Reagents.
1. PLURONIC® F68
    BASF Corp., Florham Park, N.J.
2. PLURONIC® F127
    BASF Corp., Florham Park, N.J.
3. Perfluorotributylamine
    e.g., FLUORINERT™ FC-43, 3M, St. Paul, Minn.
4. Hank's Balanced Salt Solution w/o Ca+ or Mg+ ("HBSS")
    e.g., CELLGRO® by Mediatech, Inc., Manassas, Va.
5. Isoflurane (clinical grade)

Equipment.
1. 1 L beaker
2. 500 mL filter flask
3. 50 cc conical tube
4. Ice and bucket
5. Plunger pipettor and tips
6. High Pressure Microfluidizer Processor—Model M-110Y Microfluidics Int'l. Corp., Newton, Mass.

Preparation.
A surfactant solution is initially prepared by weighing out 16.665 g each of PLURONIC® F68 and PLURONIC® F127, ethylene oxide/propylene oxide block copolymers, and adding the amounts of each block copolymer to 480 mL of sterile HBSS, without calcium or magnesium, in a sterile 1 L beaker with a stir bar, and covering the beaker. Initiate mixing at medium speed so as not to cause bubble formation, and continue mixing until all of the surfactant is completely dissolved, which may require mixing overnight. Adjust the pH of the mixture to a pH of 7.35. The resultant solution will comprise the surfactants, PLURONIC® F68 and PLURONIC® F127, at a combined final concentration of 0.0333 mg/mL in PBS, i.e., a 3.33% w/v surfactant solution. The surfactant solution is then filtered via a 500 mL sterile filter flask.

A stable liquid emulsion containing 10.0% sevoflurane, by volume, is prepared by adding 30 mL of a 3.33% surfactant solution, prepared in accordance with the procedures of the preceding paragraph, and 10 mL of HESS solution, without calcium or magnesium, in a 50 cc conical glass tube fitted with a TEFLON® stopper.

The high pressure microfluidizer processor ("HPMP") is prepressurized to about 100 pounds per square inch ("psi"). An amount of approximately 200 mL of sterile HESS without calcium or magnesium is added to the inlet reservoir of the unit, and the HPMP is activated and primed with about 50 mL of HESS. The cooling chamber of the HPMP is filled with an ice water slurry. Optionally, an amount of ethanol may be added to the ice water slurry to super cool the solution.

Continue operating the HPMP at low pressure until the inlet reservoir is almost empty. Add the 40 mL surfactant/HESS solution, previously prepared, to the inlet chamber of the HPMP, and adjust the pressure of the HPMP until to about 5,000 psi. Operate the HPMP for 3 cycles to clear the lines and discard the output solution, approximately 15 mL.

Reroute the product outlet line of the HPMP to the inlet reservoir of the unit, and adjust pressure, as needed, to 5,000 psi. Add 5 mL of perfluorotributylamine (FLUORINERT™ FC-43) into the inlet reservoir with a plunger pipettor, and then add 5 mL of liquid isoflurane to the inlet reservoir via the plunger pipettor, and activate the HPMP at 5,000 psi. The HPMP is operated for a period of 8 minutes, with the solution recirculated through the unit from the product outlet line into the inlet reservoir. Samples are intermittently drawn off from the product outlet line to check for uniformity and clarity of the emulsion. The samples are returned to the inlet reservoir for further processing.

After 8 minutes of processing the solution in the HPMP at 5,000 psi, the final product, having a volume of about 50 mL, is collected in a 50 cc conical glass tube, which is capped and wrapped with PARAFILM®, to minimize gas transfer.

Example II

Measurement of Volatile Gas Anesthetic Concentration in a Stable Liquid Formulation In order to assess the stability of the liquid formulations of volatile gas anesthetics prepared in accordance with the procedures presented above in Example I, several methods were developed to permit the measurement of the concentration of a volatile gas anesthetic present in a liquid solution, such as an emulsion or nanoemulsion.

A. Volatile Gas Anesthetic Concentration Measurement by HPLC.

The method was utilized to measure the concentration of volatile gas anesthetic in each of the nanoemulsions prepared in accordance with the procedures presented above in an Examples I-A and I-B via high performance liquid chromatography ("HPLC") utilizing a LaChrom Elite system, as manufactured by Hitachi High Technologies America Corporation of Schaumburg, Ill. More in particular, the concentration of volatile gas anesthetic in the aforementioned nanoemulsions was measured under various storage conditions, namely, open and exposed to ambient air at 25° C. and 37° C., in order to emulate the environment inside of a tissue culture incubator, as well as being closed to ambient air at temperatures of 4° C. and 25° C.

In accordance with the present example, 100 microliters ("µL") of a nanoemulsion initially containing an amount of 4.5% by volume of the volatile gas anesthetic isoflurane prepared in accordance with the procedure present above in Example I-A, was added to a glass vial containing 500 µL of n-heptane, Sigma-Aldrich Co., St. Louis, Mo., and the glass vial was sealed with a TEFLON® cap. Another 100 µl of the same nanoemulsion was added to 500 µl of an internal standard halothane Sigma-Aldrich Co., St. Louis, Mo., and the glass vial was sealed with a TEFLON® cap. Each of the glass vials was vortexed for 1 minute in order to extract isoflurane into the organic phase, i.e., either into the n-heptane layer or the halothane layer. After vortexing, each of the vials were centrifuged at 2,000 revolution per minute ("rpm") for a period of 3 minutes in order to completely separate the phases. A portion of the organic phase from each glass vial was transferred into a separate HPLC vial insert, and 100 μl of each portion was subsequently injected into a NOVA-PAK® C18, 4.6×150 mm HPLC column, Waters Corporation, Milford, Mass. The detector wavelength was set at 210 nanometers ("nm") for the internal control standard halothane, and 203 nm for isoflurane detection. The concentration of isoflurane present in the emulsion, expressed in terms of weight percent, was then calculated from the area ratio of isoflurane to halothane and compared to the standard calibration curves prepared from known amounts of isoflurane.

FIG. 10 is a graphical representation of known isoflurane concentrations versus the area under curve of the isoflurane peak as measured by HPLC in accordance with the foregoing method.

B. Volatile Gas Anesthetic Concentration Measurement by Weight.

A standard curve for determining isoflurane concentration was generated based upon 1 mL mixtures of a base solution, i.e., 2% w/v surfactant plus PBS or HBSS; 10% v/v FC-43; and, various known v/v % isoflurane concentrations. A 1 mL aliquot of each of these mixtures was weighed and compared to its expected weight based on the density of each component, and a predicted density of each mixture. The predicted or expected density of each mixture was determined by the following equation:

$$\rho_{expected} = v\%_A * \rho_A + v\%_B \rho_B + v\%_C \rho_C$$

where ρ is the density, and A, B, C are the surfactant solution, PCF or FC-43, and isoflurane, respectively. FIG. 8 is a standard curve generated in accordance with the procedure of this example for the determination of isoflurane concentration by weight. The measured values were compared to the theoretical values, or $\rho_{expected}$, and a high degree of correlation, $R^2 > 0.99$, was observed, as illustrated in FIG. 9.

From the standard curve generated of the mixtures, the content of isoflurane in any emulsion can be determined by weighing a known volume, for example, a 1 mL aliquot. and tabulating the known portions of the weight, e.g., the volume percentages of the base solution and PCF, i.e., FC-43, and calculating the unknown volume by dividing the remaining weight by the density of pure isoflurane. The following equation describes this relationship:

$$v_{isoflurane} = (\omega_{total} - (\rho_{base} * v\%_{base} + \rho_{PCF} * v\%_{PCF}))/\rho_{isoflurane}$$

C. Volatile Gas Anesthetic Concentration Measurement by ATR-FTIR.

Attenuated total reflectance Fourier transform infrared spectroscopy, or ATR-FTIR, is a technique that provides information about the chemical bonding or molecular structure of materials, whether organic or inorganic. The technique works on the fact that bonds and groups of bonds vibrate at characteristic frequencies. A molecule that is exposed to infrared rays absorbs infrared energy at frequencies which are characteristic to that molecule. During ATR-FTIR analysis, a spot on a specimen is subjected to a modulated infrared ("IR") light beam. The specimen's transmittance and reflectance of the infrared rays at different frequencies is translated into an IR absorption plot consisting of reverse peaks.

ATR-FTIR analysis was performed on a perfluorocarbon, specifically, perfluorotributylamine (FLUORINERT™ FC-43 or FC-43), a base solution (PBS+surfactant), isoflurane, and a base solution (PBS+surfactant) with 10% FC-43, and the unique peaks of isoflurane were characterized which allows quantification of the isoflurane content based on measurements of areas under the spectral peaks from the ATR-FTIR plots.

In accordance with the present example, ATR-FTIR spectra were recorded on a PerkinElmer Spectrum 100 FTIR spectrometer equipped with a KBr beam splitter, 1 bounce Universal Di/ZnSe ATR sampling accessory, and electronically, temperature-stabilized fast recovery deuterated triglycine sulfate detector. The spectra generated are an average of four scans at a resolution of 4 cm$^{-1}$. Emulsion samples of 50 μL each were obtained from each of the emulsions described below, and the emulsion samples were measured by covering the measurement surface. Standard curves were generated by manufacturing emulsions of known volume percentage isoflurane by gravimetric determination, performing ATR-FTIR measurements and then, taking area under the curve ("AUC") determinations of peaks in the region specific to fluorine bond vibration (1300-1000 cm$^{-1}$). Additionally, ATR-FTIR and AUC measurements were also performed on the base surfactant solution, i.e., a 0% standard, and pure isoflurane, i.e., a 100% standard.

A series of 50 mL emulsions were prepared having a constant FLUORINERT™ FC-43 content (10% v/v FC-43) with varying isoflurane content (5%, 10% and 20% v/v). The emulsions were prepared by first adding an amount of surfactant solution to an appropriate volume for each sample, specifically, 42.5 mL in a 5% isoflurane emulsion; 40 mL in a 10% isoflurane emulsion; and, 35 mL in 20% isoflurane emulsion. Next, 5 mL of FC-43 was added to each solution which remains phase separated, due to density, at the bottom of the conical tube. Finally, appropriate volumes of isoflurane, specifically, 2.5 mL in the 5% emulsion; 5 mL in the 10% emulsion; and, 10 mL in the 20% emulsion, were added to the corresponding sample tube. The isoflurane also sinks to the bottom of the conical tube and remains phase separated due to density and hydrophobicity, however, the isoflurane mixes completely with the FC-43 in the bottom of the conical tube. The sample solution were emulsified via high pressure microfluidization for 8 minutes at 6000 PSI under ice slurry cooling, similar to the procedure outlined in Example I-C above. At the completion of the emulsification, the full sample volume was collected in a corresponding conical tube and sealed.

ATR-FTIR was performed in triplicate on each of the aforementioned sample emulsions, mixing each sample well before each measurement and sealing immediately after extracting each sample for analysis. A nice spectral peak increase was observed relative to the 0% isoflurane control, i.e., 10% FC-43 emulsion with no isoflurane, in two spectral regions, specifically, 1300-1260 cm$^{-1}$ and 1225-1011 cm$^{-1}$. The images of the spectra for the spectral region 1300-1260 cm$^{-1}$ are presented in FIG. 14, and FIG. 15 presents the spectra for the region 1225-1011 cm$^{-1}$.

From these peaks, measurements of the area under the curve ("AUC") for each of the two spectral regions, once again, 1300-1260 cm$^{-1}$ and 1225-1011 cm$^{-1}$, were used to generate standard curves of isoflurane concentration. Two types of standard curves were generated. First, a two point standard curve was generated between 0% and 100% isoflurane concentrations which are compared to a second five point standard curve containing theoretical emulsion concentrations. The two curves were generated to evaluate the possibility of isoflurane loss during the emulsification process, as a comparison between the two standard curves would allow for assessment of error in emulsion manufacture and allow for more accurate quantification. FIG. 16 presents the standard curves generated for the determination of isoflurane concentration for the spectral region of 1300-1260 cm$^{-1}$ by ATR-FTIR, and FIG. 15 presents the standard curves generated for the determination of isoflurane concentration for the spectral region of 1225-1011 cm$^{-1}$ by ATR-FTIR.

Next, an assessment of standard curve accuracy was performed by comparing the theoretical isoflurane values against the calculated values in each spectral standard curve generated by ATR-FTIR. These results are presented in FIGS. 18 and 19. An ideal curve would have a slope approximating unity with a minimal y intercept.

As may be seen from FIGS. 18 and 19, All of the standard curve are within 6% of unity with the majority being <<1% difference from unity. This fact, combined with the data presented in FIGS. 14 through 17, demonstrates the robustness of the present method in accurately calculating the isoflurane concentration in emulsions. In one further embodiment of the present method, the two point curve is used until more "n" can be generated to bolster the 5 point curve. Additionally, the measurements from the spectral range of 1300-1260 cm$^{-1}$ appear to be the most accurate in determining isoflurane concentration.

Using the standard curve for the spectral range of 1300-1260 cm$^{-1}$, a time course study was performed on a 20% isoflurane emulsion read continuously in one minute intervals to observe the volatility of isoflurane within the emulsion when exposed to air. It should be noted that pure isoflurane evaporated completely within 10 seconds of addition to ATR-FTIR crystal and had to be continuously added to get a reading for 100%. The AUC were collected and used to calculate the percentage of isoflurane remaining over time. Next, best fit models were calculated based on the data, and were observed to follow a plateau followed by exponential decay model. The modeled curves are plotted along with the measured values which, as can be seen from FIG. 20, are in close agreement with the measured values wherein $R^2$=0.99 and 0.98, respectively.

As shown in FIG. 20, measurable amounts of isoflurane were completely absent within 15 minutes, although minimal isoflurane loss was observed in the first 3 minutes. This suggests the FC-43 slows the release and vaporization of the isoflurane, but does not prevent it from achieving its effective gaseous state.

Example III

Stability of Liquid Formulations of Volatile Gas Anesthetics

A. Concentration of Volatile Gas Anesthetics in Liquid Formulation as Measured by HPLC.

1. Isoflurane/INTRALIPID® Based Emulsion—Open Container.

Figure 1B:
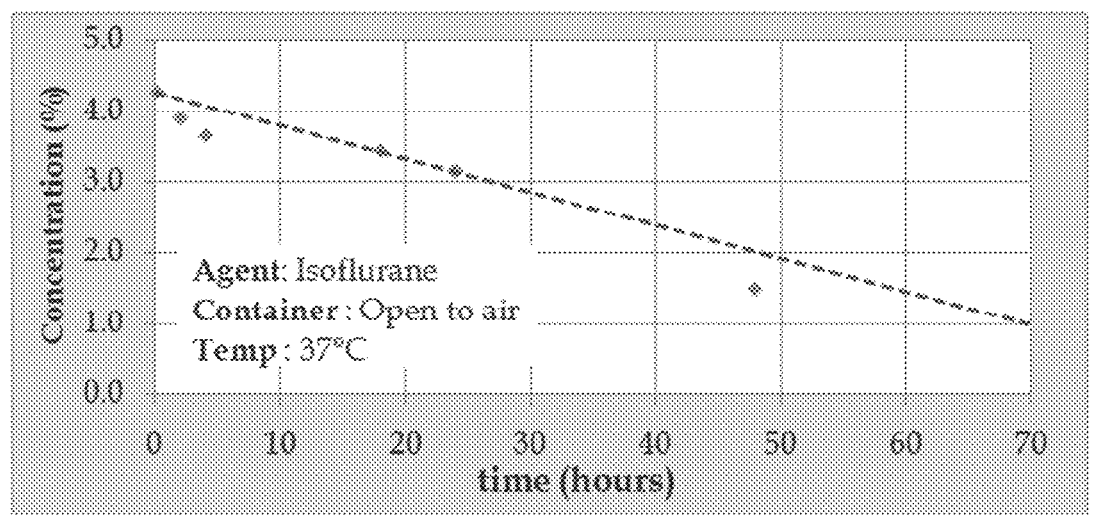
FIG. 1B is a graphical representation of isoflurane concentration versus time in a 4.5% isoflurane/INTRALIPID® based nanoemulsion prepared in accordance with an embodiment of the present invention and stored in an open container at a temperature of about 37° Celsius as measured by HPLC.

A 4.5% isoflurane/INTRALIPID® based emulsion was prepared in accordance with the procedure presented above in Example I-A. Portions of the emulsion were stored in open containers and exposed to ambient air at temperatures of 25° C., to approximate room temperature, and 37° C., to approximate human body temperature, and periodic samples were withdrawn and analyzed in accordance with the procedure identified in Example II-A above. FIGS. 1A and 1B illustrate the results of these tests with isoflurane concentration, in weight percent, along the y-axis, and time, in hours, along the x-axis of each these figures.

As illustrated in FIG. 1A, the portion of the 4.5% isoflurane/INTRALIPID® based emulsion retained about 93% of its original concentration of isoflurane while stored in an open container at room temperature of 25° C. after 48 hours, while the portion of the 4.5% isoflurane/INTRALIPID® based emulsion stored in an open container at 37° C. retained about 33% of the original concentration of isoflurane after 48 hours, as shown in FIG. 1B. These results demonstrate that a 4.5% isoflurane/INTRALIPID® based emulsion prepared in accordance with the present invention is very stable at room temperature, i.e., approximately 25° C. As also expected, the volatile gas anesthetic in the 4.5% isoflurane/INTRALIPID® based emulsion exposed to ambient air evaporates over time at body temperature, i.e., approximately 37° C., as this temperature is well above the latent heat of vaporization of isoflurane.

2. Isoflurane/INTRALIPID® Based Emulsion Closed Container.

Figure 2A:
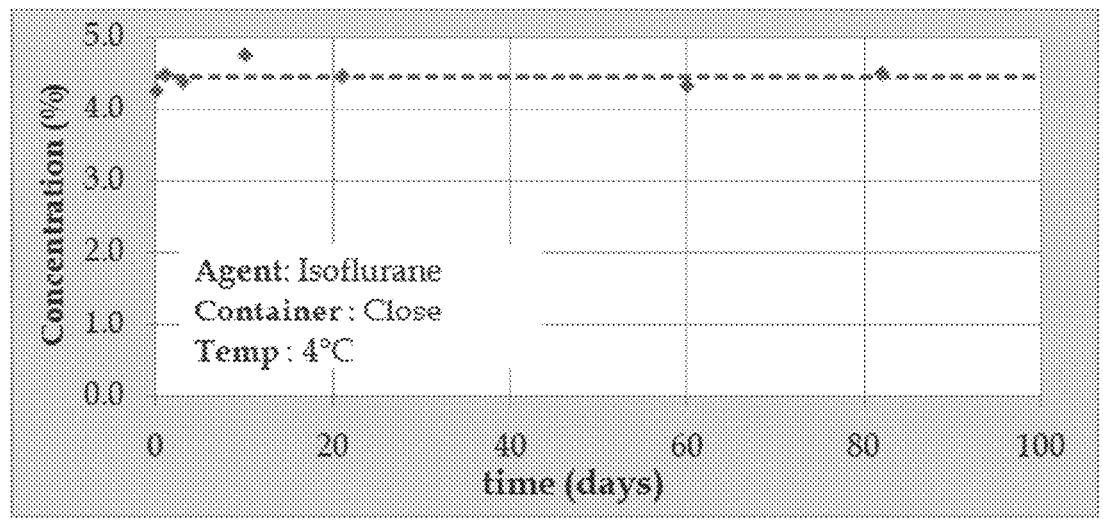
FIG. 2A is a graphical representation of isoflurane concentration versus time in a 4.5% isoflurane/INTRALIPID® based nanoemulsion prepared in accordance with an embodiment of the present invention and stored in a closed container at a temperature of about 4° Celsius as measured by HPLC.
Figure 2B:
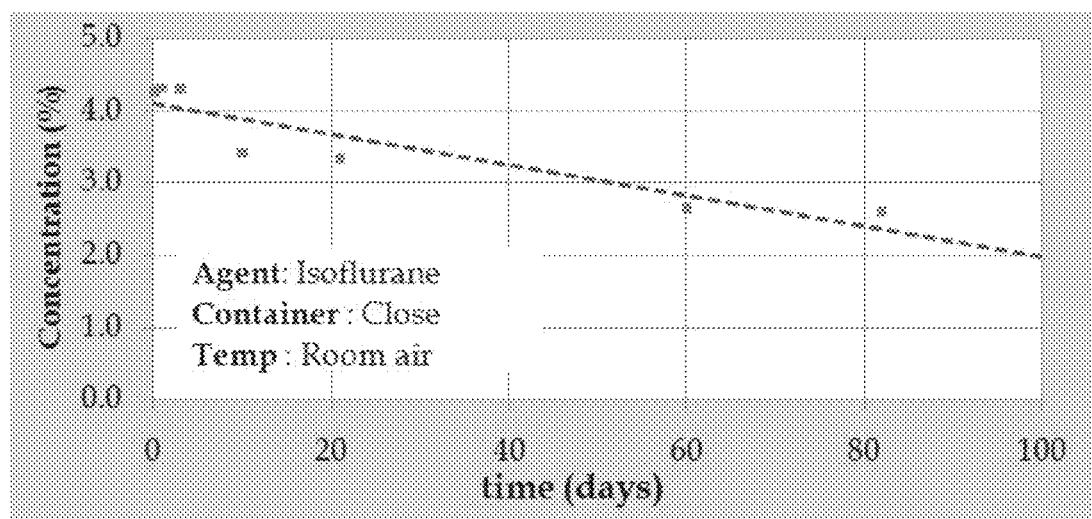
FIG. 2B is a graphical representation of isoflurane concentration versus time in a 4.5% isoflurane/INTRALIPID® based nanoemulsion prepared in accordance with an embodiment of the present invention and stored in a closed container at a room temperature of about 25° Celsius as measured by HPLC.

A 4.5% isoflurane/INTRALIPID® based emulsion was prepared in accordance with the procedure presented above in Example I-A. Portions of the emulsion were stored in containers closed to ambient air, one being refrigerated at a temperature of about 4° C., while the other was maintained at room temperature, i.e., approximately 25° C. Samples were periodically withdrawn from the containers with care taken to minimize exposure of the contents to ambient air, and analyzed in accordance with the procedure identified in Example II-A above. FIGS. 2A and 2B illustrate the results of these tests with isoflurane concentration, in weight percent, along the y-axis, and time, in days, along the x-axis of each these figures. FIG. 2Av2 is an alternate graphical representation of the data presented in FIG. 2A.

As illustrated in FIGS. 2A and 2Av2, the portion of the 4.5% isoflurane/INTRALIPID® based emulsion retained greater than 99% of its original concentration of isoflurane while stored in a closed container at a refrigerated temperature of 4° C., even when tested after more than 80 days. Further, FIG. 2B shows that even at room temperature the 4.5% isoflurane/INTRALIPID® based emulsion retained about 60% of its original concentration of isoflurane while stored in a closed container at room temperature of about 25° C.

These results demonstrate that a 4.5% isoflurane/INTRALIPID® based emulsion prepared in accordance with the present invention is extremely stable when stored in a closed container and refrigerated, which is common practice for many pharmaceutical and other therapeutic agents. Further, even at room temperature, the tests results demonstrate that the 4.5% isoflurane/INTRALIPID® based emulsion is reasonably stable when stored in a closed container at room temperature over extended periods of time.

3. Sevoflurane/INTRALIPID® Based Emulsion—Open Container.

Figure 3A:
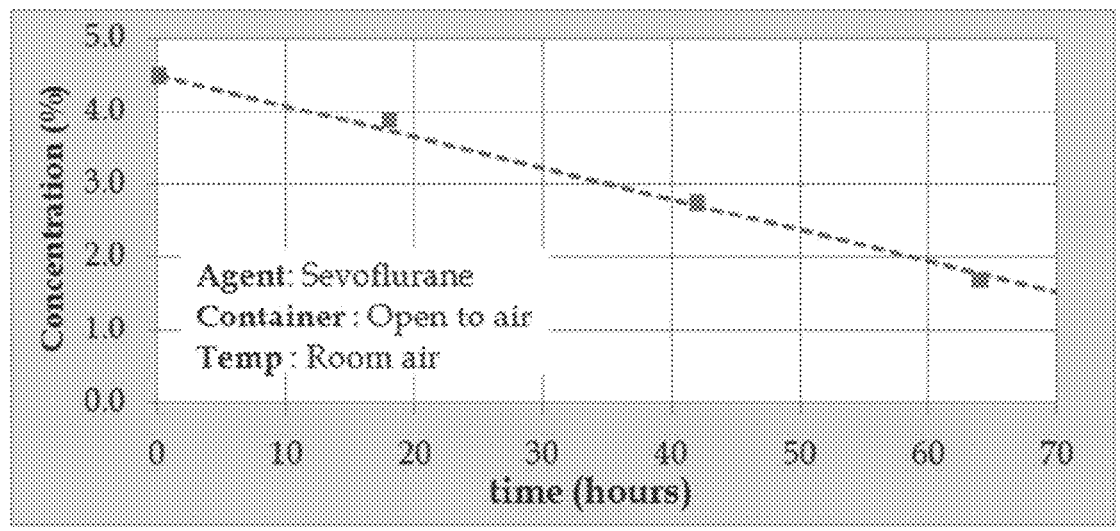
FIG. 3A is a graphical representation of sevoflurane concentration versus time in a 4.5% sevoflurane/INTRALIPID® based nanoemulsion prepared in accordance with an embodiment of the present invention and stored in an open container at a room temperature of about 25° Celsius as measured by HPLC.
Figure 3B:
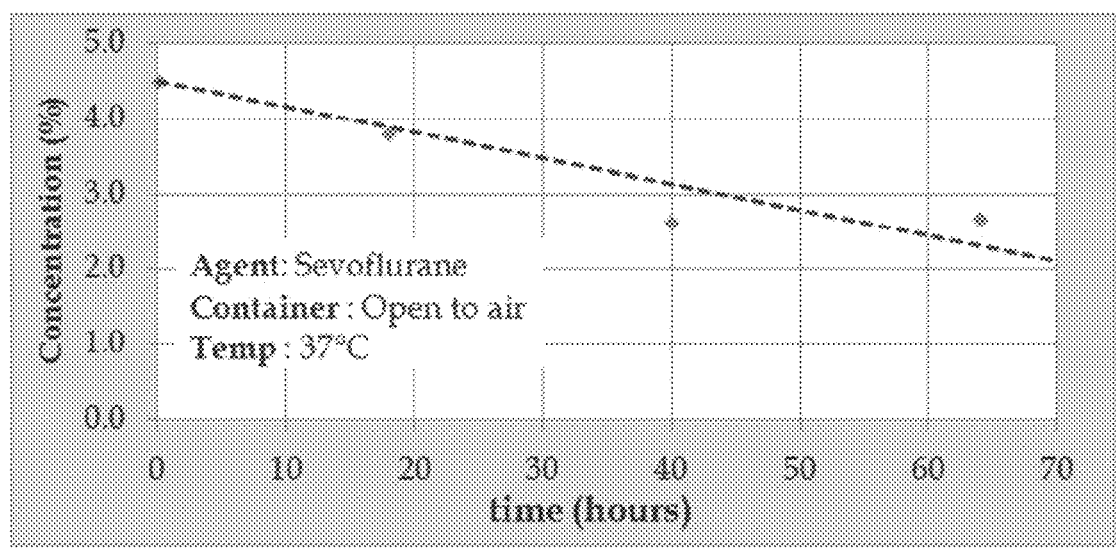
FIG. 3B is a graphical representation of sevoflurane concentration versus time in a 4.5% sevoflurane/INTRALIPID® based nanoemulsion prepared in accordance with an embodiment of the present invention and stored in an open container at a temperature of about 37° Celsius as measured by HPLC.

A 4.5% sevoflurane/INTRALIPID® based emulsion was prepared in accordance with the procedure presented above in Example I-B. Portions of the emulsion were stored in open containers and exposed to ambient air at temperatures of 25° C., to approximate room temperature, and 37° C., to approximate human body temperature, and periodic samples were withdrawn and analyzed in accordance with the procedure identified in Example II-A above. FIGS. 3A and 3B illustrate the results of these tests with sevoflurane concentration, in weight percent, along the y-axis, and time, in hours, along the x-axis of each these figures.

As illustrated in FIG. 3A, the portion of the 4.5% sevoflurane/INTRALIPID® based emulsion retained about 86% of its original concentration of sevoflurane while stored in an open container at room temperature of 25° C. for 18 hours, while the portion of the 4.5% sevoflurane/INTRALIPID® based emulsion stored in an open container at 37° C. retained about 84% of the original concentration of sevoflurane after 18 hours, as shown in FIG. 3B.

These results show that the stability of a 4.5% sevoflurane/INTRALIPID® based emulsion prepared in accordance with the present invention is similar to the stability of a 4.5% isoflurane/INTRALIPID® based emulsion, i.e., very stable at room temperature, and superior to the 4.5% isoflurane/INTRALIPID® based emulsion with respect to stability at body temperature while exposed to ambient air. Based on these results, it is expected that a 4.5% sevoflurane/INTRALIPID® based emulsion prepared in accordance with the present invention will exhibit similar or better shelf life stability compared to a 4.5% isoflurane/INTRALIPID® based emulsion.

B. NanoParticle Size Distribution of Volatile Gas Anesthetics in Liquid Formulation.

1. Isoflurane/INTRALIPID® Based Emulsion—Closed Container.

A 4.5% isoflurane/INTRALIPID® based emulsion was prepared in accordance with the procedure presented above in Example I-A, and one sample were stored in closed containers at a refrigerated temperature of 4° C., while another sample was stored in a closed container at a room temperature of 25° C., respectively. The nanoparticle size distribution of the emulsion samples was measured utilizing a DynaPro Titan Dynamic Light Scattering instrument, as manufactured by Wyatt Technology Corporation, Santa Barbara, Calif.

Figure 4:
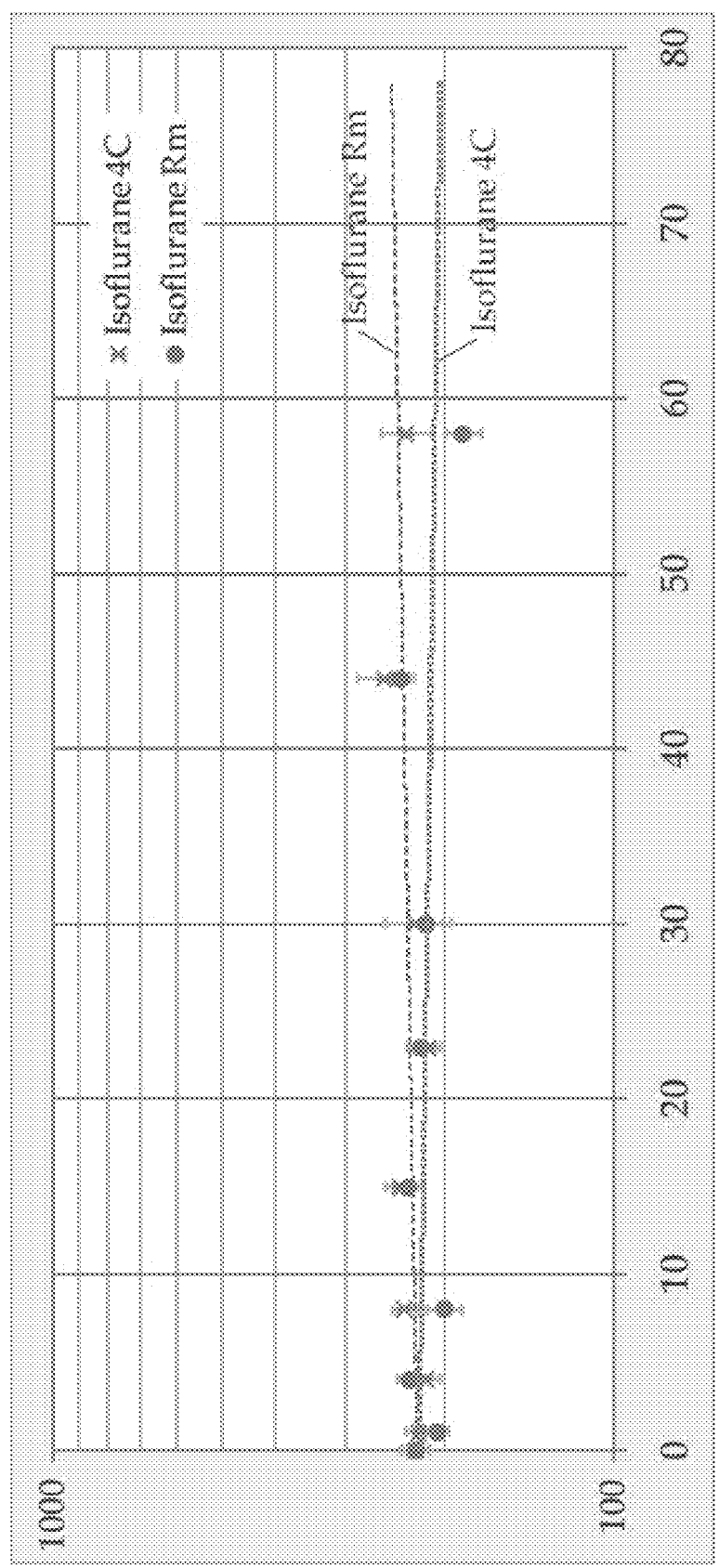
FIG. 4 is a graphical representation of nanoparticle size distribution versus time in a 4.5% isoflurane/INTRALIPID® based nanoemulsion prepared in accordance with an embodiment of the present invention and stored in a closed container at temperatures of about 4° Celsius and 25° Celsius as measured by direct light scattering.

The nanoparticle size distribution of the 4.5% isoflurane/INTRALIPID® based emulsion was 451.7±24.6 nm in the initial samples. After 58 days stored in a closed container, the nanoparticle size distribution was 469.5±49.1 nm at 4° C., and 371.3±27.8 nm at 25° C., as is illustrated in FIG. 4. FIG. 4A is illustrative of similar results obtained from a subsequent sample of a 4.5% isoflurane/INTRALIPID® based emulsion prepared in accordance with the present invention.

These results demonstrate that a 4.5% isoflurane/INTRALIPID® based emulsion prepared in accordance with the present invention is very stable when stored in a closed container, even at room temperature.

2. Sevoflurane/INTRALIPID® Based Emulsion Closed Container.

A 4.5% sevoflurane/INTRALIPID® based emulsion was prepared in accordance with the procedure presented above in Example I-B, and one sample was stored in closed containers at a refrigerated temperature of about 4° C., while another sample was stored in a closed container at a room temperature of 25° C., respectively. The nanoparticle size distribution of the emulsion samples was measured utilizing a DynaPro Titan Dynamic Light Scattering instrument, as manufactured by Wyatt Technology Corporation, Santa Barbara, Calif.

Figure 5:
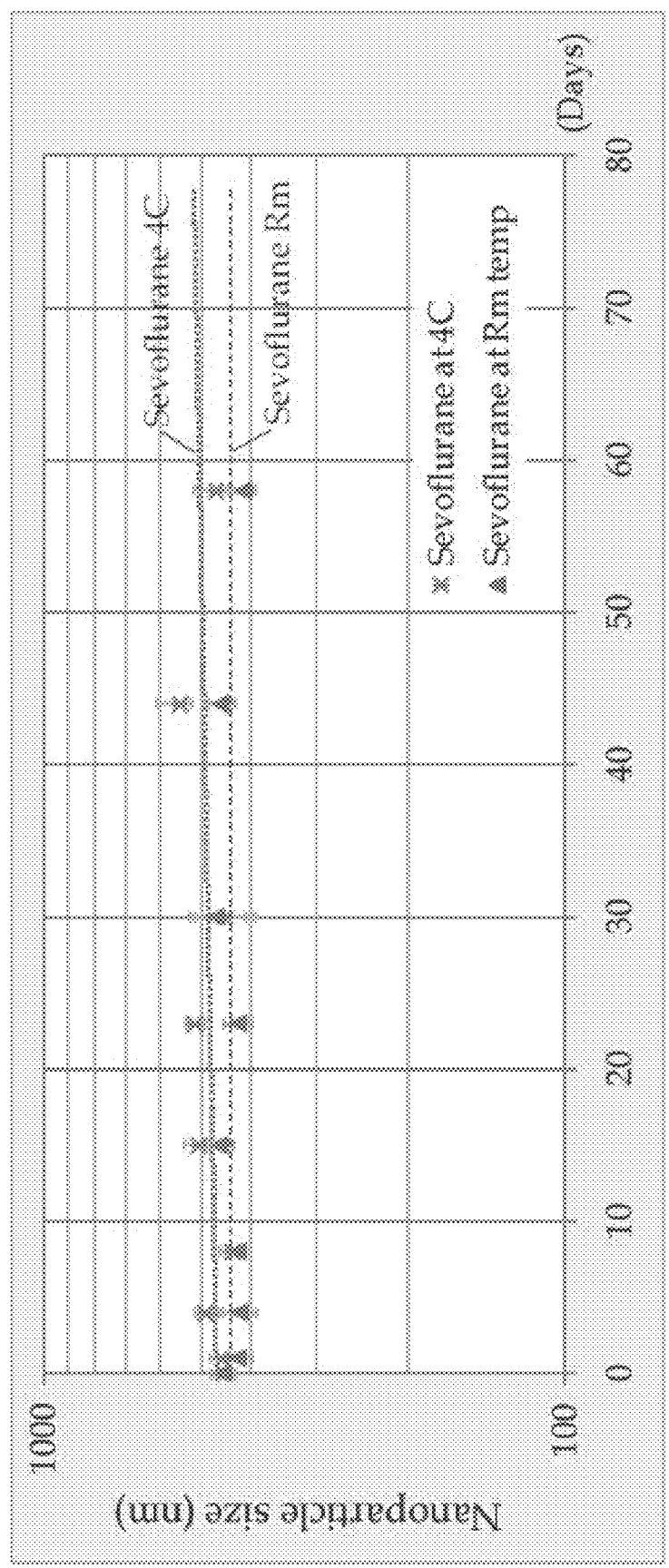
FIG. 5 is a graphical representation of nanoparticle size distribution versus time in a 4.5% sevoflurane/INTRALIPID® based nanoemulsion prepared in accordance with an embodiment of the present invention and stored in a closed container at temperatures of about 4° Celsius and 25° Celsius as measured by direct light scattering.

The nanoparticle size distribution of the 4.5% sevoflurane/INTRALIPID® based emulsion was 453.1±23.3 nm in the initial samples. After 58 days stored in a closed container, the nanoparticle size distribution was 465.3±37.8 nm at 4° C., and 415.2±20.9 nm at 25° C., as is illustrated in FIG. 5.

These results further demonstrate that a 4.5% sevoflurane/INTRALIPID® based emulsion prepared in accordance with the present invention is also very stable when stored in a closed container, once again, even at room temperature.

C. Concentration of Volatile Gas Anesthetics in Liquid Formulation as Measured by Weight.

As discussed in Example II-B above, based on the standard curve generated and presented in FIG. 8 the content of isoflurane in any emulsion can be determined by weighing a known volume, for example, a 1 mL aliquot, tabulating the known portions of the weight, e.g., the volume percentages of the base solution and FC-43, and calculating the unknown volume by dividing the remaining weight by the density of pure isoflurane. Once again, the following equation describes this relationship:

$$v_{isoflurane} = (\omega_{total} - (\rho_{base} * v\%_{base} + \rho_{PCF} * v\%_{PCF})) / \rho_{isoflurane}$$

This method of measuring isoflurane concentration by weight was applied to various exemplary nanoemulsions prepared in accordance with the methods of the present invention, and the results are presented graphically herein in FIGS. 11 through 13.

To begin, FIG. 11 demonstrates the considerable stability of a 4.5% isoflurane/INTRALIPID® nanoemulsion as compared to pure isoflurane, even when stored in an open container at room temperature of about 21° C. Looking to FIG. 11, nearly 50% of the pure isoflurane sample had evaporated after only about 0.2 hours, and the pure isoflurane sample had essentially completely evaporated in a little over 0.5 hours. Conversely, about 70% of the isoflurane in the original 4.5% nanoemulsion remained even after a full one hour exposure in an open container at room temperature of about 21° C.

FIG. 12 presents the results for a 4.5% isoflurane/INTRALIPID® nanoemulsion stored in an open container at room temperature of about 21° C. for a period of 24 hours. As in FIG. 11, after one hour, about 70% of the original amount of isoflurane remained in the nanomulsion, and after a full 24 hours of exposure to room temperature in open container, the concentration of isoflurane in emulsion was still greater than 1%.

Of course, in practice, a nanoemulsion comprising a volatile gas anesthetic prepared in accordance with the present invention would likely be stored in a closed container, and under at least moderate refrigeration. As such, a further test was performed on a 4.5% isoflurane/INTRALIPID® nanoemulsion stored in a closed container at a temperature of about 4° C. for a period of seven days. As the results presented in FIG. 13 demonstrate, the 4.5% isoflurane/INTRALIPID® nanoemulsion prepared in accordance with the present invention was extremely stable over the entire seven day test period, with negligible loss of isoflurane observed.

D. Concentration of Volatile Gas Anesthetics in Liquid Formulation as Measured by ATR-FTIR.

Storage stability studies over time in days were performed on samples of 10% and 20% isoflurane emulsions in FLUORINERT™ FC-43, prepared in accordance with the method presented in Example II-C above. The samples were stored in open containers at a room temperature of about 25° C. throughout the study, and the percentage of isoflurane was measured every day for six (6) days via ATR-FTIR for the spectral range of 1300-1260 cm$^{-1}$. The results of this study are presented in FIG. 20A.

As may be seen from FIG. 20A, both the 10% and 20% isoflurane emulsions in FLUORINERT™ FC-43 exhibited minimal loss of isoflurane concentration over the test period. Specifically, the concentration of the 10% sample decreased to about 8%, while the concentration of the 20% sample decreased by less than 10% of its original concentration. Thus, this study further demonstrates and corroborates the stability of isoflurane emulsions prepared in accordance with the present invention, even when stored in an open container at room temperatures.

Example IV

In Vivo Testing of the Efficacy of Stable Liquid Formulations of Volatile Gas Anesthetics Stable liquid formulations of volatile gas anesthetics prepared in accordance with the present invention were tested in vivo in rodents, to assess the anesthetic/sedative properties, and to determine acceptable dosages. More in particular, increasing dosages of stable liquid formulations of volatile gas anesthetics of the present invention were administered to male Lewis rats via intravenous injection through an internal jugular catheter ("IJC") implanted within a week prior to testing.

The primary test endpoints included: (i) achievement of sleep/unresponsiveness, i.e., anesthesia; (ii) achievement of effective analgesia; and, (iii) mortality. Several parameters were measured as a baseline prior to the administration of the test formulation, and once again following the induction of anesthesia, including: (i) time to induction; (ii) duration of the deep anesthesia/sedation after administration of a bolus dose of the formulation; and, (iii) response to painful stimuli, such as, tail clamping or forepaw righting reflex.

Following the induction of anesthesia, the rats were observed to measure the time required to recover from anesthesia and regain reflexes. Additional parameters measured during the tests include: (i) oxygen saturation; (ii) heart rate; and (iii) respiratory rate, using a noninvasive monitoring instrument, e.g., a MouseOx® monitoring system, STARR Life Sciences Corp., Oakmont, Pa.; (iv) exhaled anesthetic concentrations; and, (v) exhaled oxygen concentrations, via a mask or tracheal tube.

A. 4.5% Isoflurane/INTRALIPID® Based Emulsion.

Five male Lewis rats weighing 250 to 300 g each were used for in vivo experiments. The rats were weighed before testing, and the dosage of the test formulation to be administered to each was determined based on the weight. A 4.5% isoflurane/INTRALIPID® based emulsion was prepared in accordance with the procedure of Example I-A, immediately prior to testing and was refrigerated until ready for use. The isoflurane/INTRALIPID® emulsion was warmed to room temperature before injection. A 3 mL PVC syringe was filled with the isoflurane/INTRALIPID® emulsion and set onto the infusion pump. After flushing the IJC connector with saline, the isoflurane/INTRALIPID® emulsion was aspirated into the extension catheter and connected to the IJC connector. Injection parameters included a total injection volume of 0.09 mL of pure isoflurane/kg, at a rate of injection of 0.513 mL/min of the 4.5% isoflurane/INTRALIPID® based emulsion. Immediately after administration of the full dosage of the test formulation, each of the rats became anesthetized and unresponsive to painful stimuli, i.e., tail vein clamping. After discontinuation of infusion, each of the rats slowly emerged from general anesthesia and became responsive to tail vein clamping within 7 minutes from injection time. Rats were observed for several hours after complete recovery from anesthesia. There were no significant clinical signs of toxicity noticed at doses studied.

Figure 6:
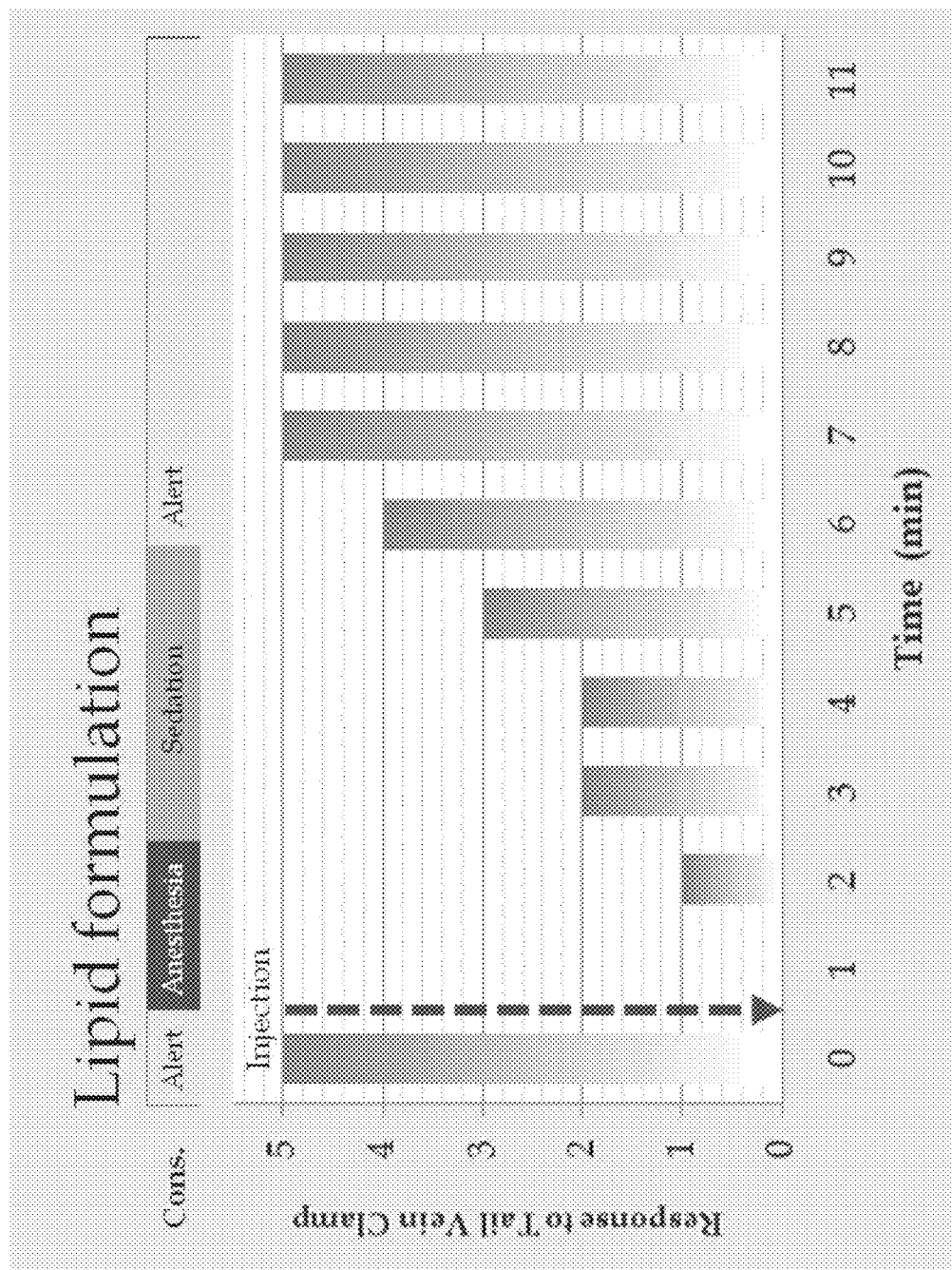
FIG. 6 is a graphical representation of the response of male Lewis rats to a tail vein clamp versus time immediately preceding and following administration of an injection of a 4.5% isoflurane/INTRALIPID® based nanoemulsion prepared in accordance with an embodiment of the present invention.

FIG. 6 is graphical representation of the results of the in vivo testing conducted on male Lewis rats utilizing a 4.5% isoflurane/INTRALIPID® based emulsion prepared in accordance with the procedures of the present invention.

B. Isoflurane/Non-Lipid Based Emulsion.

Five different male Lewis rats weighing 250 to 300 g were used for additional in vivo experiments. As in the previous testing regimen, the rats were weighed before testing, and the dosage of the test formulation to be administered to each was determined based on the weight. A 10% isoflurane/non-lipid based emulsion was prepared immediately before experiments in accordance with the procedure outlined in example I-C above, and stored at room temperature. A 3 mL PVC syringe was filled with the isoflurane/non-lipid based emulsion and set into the infusion pump. After flushing the IJC connector with saline, a catheter filled with the isoflurane/non-lipid based emulsion was connected to the IJC connector. Injection parameters comprised an injection volume of 0.23 mL/kg of the 10% isoflurane/non-lipid emulsion at a rate of injection of 1.32 mL/min.

Within 3 minutes of administration of the full dosage of the test formulation, all of the rats were anesthetized and lost forepaw-righting reflex. Upon discontinuation of the infusion, each of the rats slowly emerged from anesthesia and became responsive to tail vein clamping within 7 minutes from injection. Rats were observed for several hours after complete recovery from anesthesia. There were no significant clinical signs of toxicity observed at dosages tested.

Figure 7:
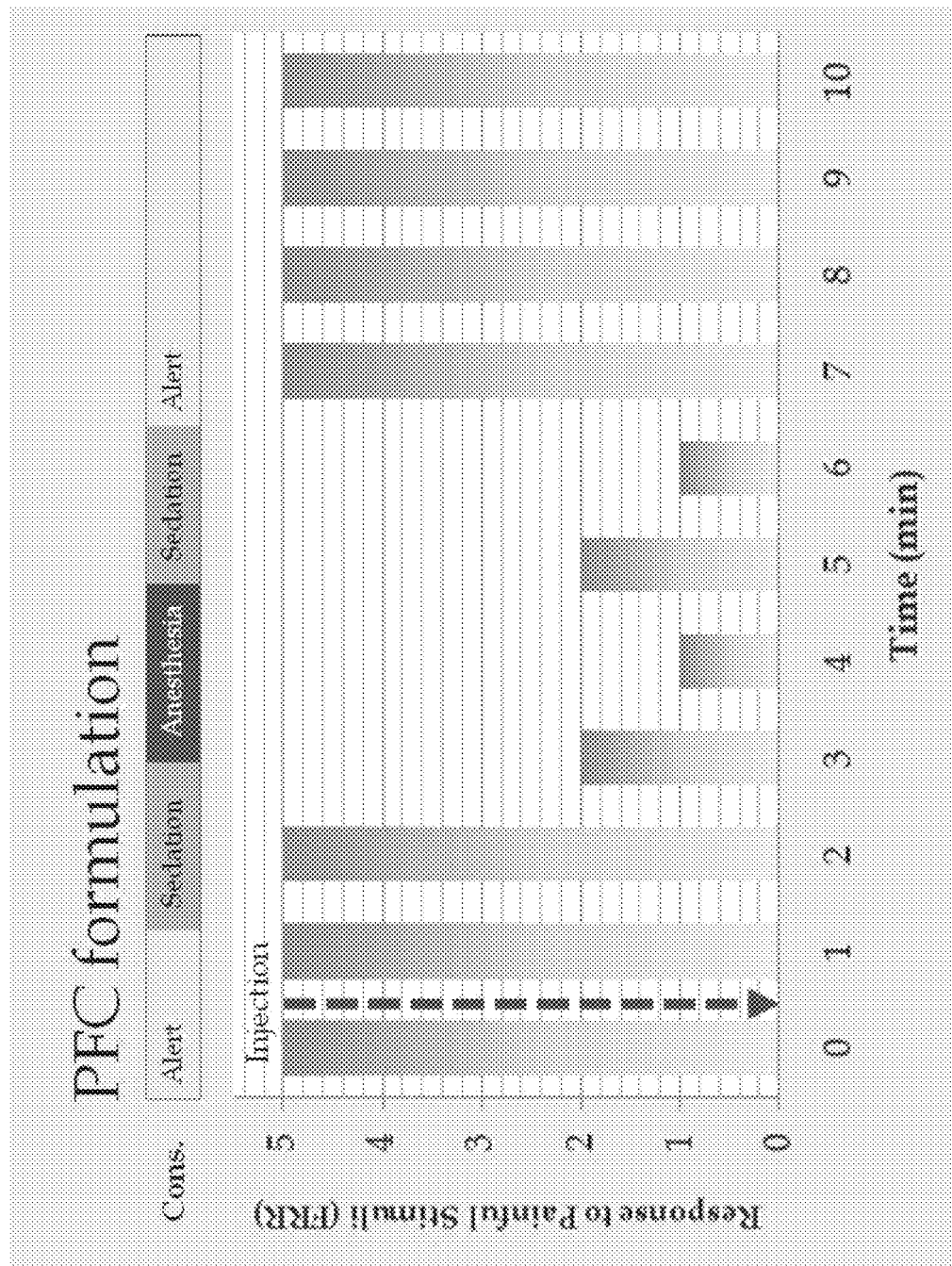
FIG. 7 is a graphical representation of the response of male Lewis rats to a tail vein clamp versus time immediately preceding and following administration of an injection of a 4.5% isoflurane/non-lipid based nanoemulsion prepared in accordance with an embodiment of the present invention.

FIG. 7 is a graphical representation of the response of male Lewis rats to a tail vein clamp versus time immediately preceding and following administration of an injection of a 4.5% isoflurane/non-lipid based nanoemulsion prepared in accordance with an embodiment of the present invention.

Example V

Determination of $ED_{50}$ and $LD_{50}$ of Stable Liquid Formulations of Volatile Gas Anesthetics Animal studies have shown that intravenously administered emulsions of volatile anesthetics may have superior preconditioning effects at lower doses than the inhaled form (Liu et al., 2004). In order to facilitate laboratory experiments aimed at studying the efficacy of volatile anesthetics to improve islet cell preservation, an ultra stable nanoemulsion of volatile anesthetic comprising 4.5% isoflurane in 30% INTRALIPID® was prepared in accordance with the procedures of the present invention. The present study was conducted to determine intravenous dosing ($ED_{50}$) and potential toxicity in rats ($LD_{50}$).

Male Lewis rats weighing 300-350 grams with previously implanted Jugular venous catheters were placed in a rodent restraint tube and preoxygenated. To determine the $ED_{50}$, groups composed of six rats each were given an infusion of the 4.5% isoflurane/INTRALIPID® nanoemulsion until the disappearance of hind paw withdrawal reflex. To determine the $LD_{50}$, groups composed of six rats each were given an infusion of the 4.5% isoflurane/INTRALIPID® nanoemulsion until cessation of respirations/death. Estimates of $ED_{50}$ and $LD_{50}$ were calculated using non-linear regression, fitting data to a sigmoidal dose-response relationship.

Logistic regression plots were drawn for $ED_{50}$ and $LD_{50}$, and are presented in FIGS. 21A and 21B, respectively. The 0.5 y-intercepts were used to calculate the $ED_{50}$ and $LD_{50}$.

As illustrated in FIG. 21A, the $ED_{50}$ of the 4.5% isoflurane/INTRALIPID® nanoemulsion is 0.073±0.003 ml/kg. The slopes of the curves for $ED_{50}$ are 41.7±9.4%*(kg/ml). The goodness of fit for $ED_{50}$ curve is $R^2$ of 0.97. FIG. 22 presents data regarding the time of loss of consciousness, loss of forepaw reflex, loss of response to tail vain clamp, and corneal reflex of the male Lewis rats of the $ED_{50}$ study immediately preceding and following administration of the injection of the 4.5% isoflurane/INTRALIPID® nanoemulsion. FIG. 23 presents data for the time and duration of induction of anesthesia, and the time of recovery of consciousness, forepaw reflex, response to tail vein clamp and corneal reflex of the male Lewis rats of the $ED_{50}$ study immediately preceding and following administration of the injection of the 4.5% isoflurane/INTRALIPID® nanoemulsion.

As illustrated in FIG. 21B, the $LD_{50}$ of the 4.5% isoflurane/INTRALIPID® nanoemulsion is 0.205±0.003 ml/kg. The slopes of the curves for $LD_{50}$ are 22.9±3.6%*%*(kg/ml). The goodness of fit for $LD_{50}$ curve is $R^2$ of 0.99. FIG. 24 is a tabulated representation of the histology of brain, heart, lung, liver and kidney of the male Lewis rats of the $LD_{50}$ study, and FIG. 25 presents a tabulated representation of biochemical markers in these rats following the $LD_{50}$ study.

This preliminary data confirms that the 4.5% isoflurane/ INTRALIPID® nanoemulsion has anesthetic potency in rats, with a margin of safety of 2.8. More in particular, the margin of safety is the ratio between a dosage that causes a lethal effect or an $LD_{50}$ and a dosage that produces a therapeutic effect, or an $ED_{50}$, and is calculated as $LD_{50}/ED_{50}$. In accordance with the present example, the $LD_{50}$ of the 4.5% isoflurane/INTRALIPID® nanoemulsion is 0.205±0.003 ml/kg, and the $ED_{50}$ of the 4.5% isoflurane/INTRALIPID® nanoemulsion is 0.073±0.003 ml/kg. Thus, the margin of safety of the 4.5% isoflurane/INTRALIPID® nanoemulsion of the present example is 0.205/0.073, or 2.8.

Example VI

Evaluation of Anesthetic Preconditioning to Protect β-Cells from Oxygen Free Radical-Induced Death Islet cell transplantation is a promising therapeutic modality for the treatment of insulin-dependent diabetes that is limited by reduced islet viability due to their susceptibility to oxidative stress during isolation. Volatile anesthetics are cytoprotective against ischemia/reperfusion injury (anesthetic pre-conditioning or APC). The present study investigated the effectiveness of Isoflurane to improve islet cell survival after induction of oxidative stress with hydrogen peroxide ($H_2O_2$).

Murine insulinoma beta-TC3 (β-TC3) cells were used as a surrogate source of β-cells in vitro. The β-TC3 cells were incubated for 48 hours, and then subdivided into four (4) groups, with three (3) series of cell cultures per group repeated in triplicate. Group 1 were sham cultured β-TC3 cells; group 2 cells were subdivided into those pre-treated with 0.5 mM isoflurane for 15 minutes or 60 minutes without $H_2O_2$, followed by an isoflurane washout; group 3 cells were exposed only to 0.3 mM $H_2O_2$ for 3 hours; group 4 cells were pre-treated with isoflurane for 15 minutes or 60 minutes, as in group 2, followed by an isoflurane washout and exposure to 0.3 mM $H_2O_2$ for 3 hours. FIG. 26 is illustrative of the experimental design for the present study.

Cells were then harvested and assayed for viability via FACS analysis (Live/Dead far red, and TMRE, mitochondrial fluorescent dye to detect apoptosis). Data was analyzed using ANOVA with post hoc Tukey for multiple comparisons.

The results of the present study are presented in FIGS. 27 and 28. As may be seen from FIG. 27, $H_2O_2$ decreased β-TC3 cell survival to 44±13% compared to controls (p<0.01). Pretreatment with isoflurane significantly improved β-TC3 cell survival compared to cells exposed to $H_2O_2$ alone, i.e., 98±2% versus 44±13% after 15 minutes, p<0.01, and; 105±0% versus 44±13%, p<0.01 after 60 minutes.

Further FIG. 28 further demonstrates that treatment by $H_2O_2$, i.e., oxidative stress, increased protein kinase activity, specifically, p38 MAPK activity. As shown in FIG. 28 pretreatment with isoflurane significantly decreased p38 MAPK activity compared to cells exposed to $H_2O_2$ alone.

The results of the foregoing experimental model show that anesthetic preconditioning of islet cells with isoflurane protects them against apoptosis by $H_2O_2$ induced oxidative stress. Since islet isolation also induces oxidative stress, isoflurane pretreatment may better preserve viability of islet cells thus reducing the amount of pancreatic tissue required and increasing the success of islet cell transplantation.

It is to be appreciated that the Detailed Description section, and not the Abstract section, is intended to be used to interpret the claims. The Abstract section may set forth one or more but not all exemplary embodiments of the present invention as contemplated by the inventor(s), and thus, are not intended to limit the present invention and the appended claims in any way.

The foregoing description of the specific embodiments should fully reveal the general nature of the invention so that others can, by applying knowledge within the skill of the art, readily modify and/or adapt for various applications such specific embodiments, without undue experimentation, without departing from the general concept of the present invention. Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents. Moreover, the breadth and scope of the present invention should not be limited by any of the above-described exemplary embodiments, but should similarly be defined only in accordance with the following claims and their equivalents.

REFERENCES

Field, J. M., Hazinski, M. F., Sayre, M. R., Chameides, L., Schexnayder, S. M., Hemphill, R., Samson, R. A., Kattwinkel, J., Berg, R. A., Bhanji, F., Cave, D. M., Jauch, E. C., Kudenchuk, P. J., Neumar, R. W., Peberdy, M. A., Perlman, J. M., Sinz, E., Travers, A. H., Berg, M. D., Billi, J. E., Eigel, B., Hickey, R. W., Kleinman, M. E., Link, M. S., Morrison, L. J., O'Connor, R. E., Shuster, M., Callaway, C. W., Cucchiara, B., Ferguson, J. D., Rea, T. D., Vanden Hoek, T. L. (2010) Part 1: executive summary: 2010 American Heart Association Guidelines for Cardiopulmonary Resuscitation and Emergency Cardiovascular Care. Circulation. 122(18 Suppl 3):S640-56.

Delgado-Escueta, A. V., Wasterlain, C., Treiman, D. M., Porter, R. J. (1982) Current concepts in neurology: management of status epilepticus. New England Journal of Medicine 306(22):1337-1340.

Eger II, E. (2004) Characteristics of anesthetic agents used for induction and maintenance of general anesthesia. *American Journal of Health System Pharmacy* 61(4):S3-S10.

Johnson, R. A., Simmons, K. T., Fast, J. P., Schroeder, C. A., Pearce, R. A., Albrecht, R. M. and Mecozzi, S. (2011) Histamine release associated with intravenous delivery of a fluorocarbon-based sevoflurane emulsion in canines. *Journal of Pharmaceutical Sciences* (Abstract) Pubmed, PMID: 21246564 [Epub ahead of print].

Lange, M., Roewer, N., Kehl, F. (2006) DEAA Anesthetic preconditioning as the alternative to ischemic preconditioning. *Journal of Thoracic and Cardiovascular Surgery* 131:252-253.

Li, Q. F., Zhu, Y. S., Jiang, H., Xu, H., Sun, Y. (2009) Heme oxygenase-1 mediates the anti-inflammatory effect of isoflurane preconditioning in LPS-stimulated macrophages. *Acta Pharmacologica Sinica* 30(2):228-234.

Liu, J., Yang, X., Ma, H., Yang, Z., Zhang, W. (2004) Comparison of MAC between intravenous injected isoflurane lipid emulsion and inhaled isoflurane in dogs. Anesthesiology 2004; 101:A127.

Lucchinetti, E., Schaub M. C., Zaugg, M. (2008) Emulsified intravenous versus evaporated inhaled isoflurane for heart protection: old wine in a new bottle or true innovation. *Anesthesia & Analgesia* 106(5):1346-1349.

MacKenzie, M. A. (1996). Poikilothermia in Man: Pathophysiological Aspects and Clinical Implications. Eisenach, J. C. (Ed.) Nifinegen University Press pg. 192.

Martinez-Arizala A., Green, B. A. (1992) Hypothermia in spinal cord injury. *Journal of Neurotrauma.* 9(Suppl 2):S497-S505.

Mosby's Pocket Dictionary of Medicine, Nursing & Allied Health, Fourth Edition. Mosby, Inc., St. Louis, Mo.

Sax, N. I. and Lewis, Sr. R. (1987) Hawley's Condensed Chemical Dictionary, Eleventh Edition. Van Nostrand Reinhold, New York.

Waltman B., Scott, J. W. (1955) A study of body temperature during general anesthesia. *Canadian Anaesthetists' Society Journal* 2(2):124.

Wang, L., Traystman, R. J., Murphy, S. J. (2008) Inhalational anesthetics as preconditioning agents in ischemic brain. *Current Opinion in Pharmacology* 8(1):104-110.

The invention claimed is:

1. A method of preparing a stable liquid formulation of a volatile gas anesthetic comprising:
    adding an amount of at least one surface active agent to an amount of a buffer solution and thoroughly mixing to form a surfactant solution,
    adding an amount of a volatile gas anesthetic and an amount of a stabilizing agent comprising perfluorotributylamine to the surfactant solution, and
    emulsifying the mixture to form a stable emulsion.

2. The method as recited in claim 1 wherein the surface active agent comprises a block polymer.

3. The method as recited in claim 1 wherein the surface active agent comprises a block polymer having a hydrophobic block and at least one hydrophilic block.

4. The method as recited in claim 1 wherein the surface active agent comprises a block polymer having a central hydrophobic block and a hydrophilic block attached at either end.

5. The method as recited in claim 1 wherein the surface active agent comprises an ethylene oxide/propylene oxide block polymer.

6. The method as recited in claim 1 further comprising a plurality of surface active agents, wherein each of the plurality of surface active agents comprise comprises a different ethylene oxide/propylene oxide block polymer.

7. The method as recited in claim 1 wherein the buffer solution comprises a phosphate buffer solution.

8. The method as recited in claim 1 wherein the buffer solution comprises a Hank's balanced salt solution.

9. The method as recited in claim 1 wherein the volatile gas anesthetic is selected from the group consisting of isoflurane, sevoflurane, and desflurane.

10. The method as recited in claim 1 wherein emulsifying the mixture is performed via a water bath sonicator.

11. The method as recited in claim 1 wherein emulsifying the mixture is performed via a high pressure microfluidizer processor.

12. The method as recited in claim 1 wherein the stable emulsion comprises a nanoemulsion.

13. The method as recited in claim 1, comprising emulsifying the mixture for about 8 minutes.

14. The method as recited in claim 1 wherein emulsifying the mixture is performed under ice slurry cooling.

15. The method as recited in claim 1 wherein the stable emulsion comprises 10% v/v perfluorotributylamine.

* * * * *